United States Patent
Eyre et al.

(10) Patent No.: US 12,311,530 B2
(45) Date of Patent: May 27, 2025

(54) SYSTEMS AND METHODS FOR DETECTING CONTACT BETWEEN A LINK AND AN EXTERNAL OBJECT

(71) Applicant: Auris Health, Inc., Redwood City, CA (US)

(72) Inventors: Nicholas J. Eyre, Redwood City, CA (US); Alex C. Spies, Redwood City, CA (US); Colin Allen Wilson, Burlingame, CA (US); Mason Myles Markee, Pacifica, CA (US); Ying Mao, San Mateo, CA (US); Bo Yang, Mountain View, CA (US); Yanan Huang, Sunnyvale, CA (US)

(73) Assignee: Auris Health, Inc., Santa Clara, CA (US)

( * ) Notice: Subject to any disclaimer, the term of this patent is extended or adjusted under 35 U.S.C. 154(b) by 0 days.

(21) Appl. No.: 18/497,257

(22) Filed: Oct. 30, 2023

(65) Prior Publication Data
US 2024/0058970 A1  Feb. 22, 2024

Related U.S. Application Data

(63) Continuation of application No. 17/355,151, filed on Jun. 22, 2021, now Pat. No. 11,839,969.

(60) Provisional application No. 63/045,351, filed on Jun. 29, 2020.

(51) Int. Cl.
*A61B 34/30* (2016.01)
*B25J 9/00* (2006.01)
*B25J 13/08* (2006.01)

(52) U.S. Cl.
CPC ............. *B25J 13/084* (2013.01); *A61B 34/30* (2016.02); *B25J 9/0084* (2013.01)

(58) Field of Classification Search
None
See application file for complete search history.

(56) References Cited

U.S. PATENT DOCUMENTS

| | | | |
|---|---|---|---|
| 3,763,860 | A | 10/1973 | Clarke |
| 4,040,413 | A | 8/1977 | Ohshiro |
| 4,198,960 | A | 4/1980 | Utsugi |
| 4,470,407 | A | 9/1984 | Hussein |
| 4,532,935 | A | 8/1985 | Wang et al. |

(Continued)

FOREIGN PATENT DOCUMENTS

| | | |
|---|---|---|
| CN | 101443069 | 5/2009 |
| CN | 100515347 | 7/2009 |

(Continued)

OTHER PUBLICATIONS

U.S. Appl. No. 17/355,151, filed Jun. 22, 2021.
(Continued)

*Primary Examiner* — Jamel E Williams
(74) *Attorney, Agent, or Firm* — Frost Brown Todd LLP

(57) ABSTRACT

Systems and methods for detecting contact between a link and an external object are provided. In one aspect, there is provided a robotic system, including a manipulatable link, a rigid shell configured to overlay the manipulatable link, and one or more sensors positioned between the rigid shell and the manipulatable link. The one or more sensors are configured to detect contact between the rigid shell and an external object.

20 Claims, 26 Drawing Sheets

(56) References Cited

U.S. PATENT DOCUMENTS

| | | |
|---|---|---|
| 4,685,458 A | 8/1987 | Leckrone |
| 4,747,405 A | 5/1988 | Leckrone |
| 4,854,301 A | 8/1989 | Nakajima |
| 4,898,574 A | 2/1990 | Uchiyama |
| 4,983,165 A | 1/1991 | Loiterman |
| 5,029,574 A | 7/1991 | Shimamura et al. |
| 5,085,659 A | 2/1992 | Rydell |
| 5,150,452 A | 9/1992 | Pollack et al. |
| 5,196,023 A | 3/1993 | Martin |
| 5,199,417 A | 4/1993 | Muller et al. |
| 5,217,465 A | 6/1993 | Steppe |
| 5,308,323 A | 5/1994 | Sogawa et al. |
| 5,318,589 A | 6/1994 | Lichtman |
| 5,325,848 A | 7/1994 | Adams et al. |
| 5,342,381 A | 8/1994 | Tidemand |
| 5,344,395 A | 9/1994 | Whalen et al. |
| 5,353,783 A | 10/1994 | Nakao et al. |
| 5,370,609 A | 12/1994 | Drasler et al. |
| 5,372,124 A | 12/1994 | Takayama et al. |
| 5,411,016 A | 5/1995 | Kume et al. |
| 5,431,649 A | 7/1995 | Muller et al. |
| 5,441,485 A | 8/1995 | Peters |
| 5,449,356 A | 9/1995 | Walbrink et al. |
| 5,450,843 A | 9/1995 | Moll et al. |
| 5,472,426 A | 12/1995 | Bonati et al. |
| 5,496,267 A | 3/1996 | Drasler |
| 5,501,667 A | 3/1996 | Verduin, Jr. |
| 5,520,684 A | 5/1996 | Imran |
| 5,545,170 A | 8/1996 | Hart |
| 5,562,239 A | 10/1996 | Boiarski et al. |
| 5,562,648 A | 10/1996 | Peterson |
| 5,562,678 A | 10/1996 | Booker |
| 5,572,999 A | 11/1996 | Funda et al. |
| 5,573,535 A | 11/1996 | Viklund |
| 5,613,973 A | 3/1997 | Jackson et al. |
| 5,645,083 A | 7/1997 | Essig et al. |
| 5,653,374 A | 8/1997 | Young et al. |
| 5,658,311 A | 8/1997 | Baden |
| 5,695,500 A | 12/1997 | Taylor et al. |
| 5,697,949 A | 12/1997 | Giurtino et al. |
| 5,710,870 A | 1/1998 | Ohm |
| 5,716,325 A | 2/1998 | Bonutti |
| 5,737,500 A * | 4/1998 | Seraji .................. B25J 9/1643 700/262 |
| 5,788,667 A | 8/1998 | Stoller |
| 5,792,165 A | 8/1998 | Klieman |
| 5,797,900 A | 8/1998 | Madhani |
| 5,798,627 A | 8/1998 | Gilliland |
| 5,810,770 A | 9/1998 | Chin et al. |
| 5,876,325 A | 3/1999 | Mizuno et al. |
| 5,893,869 A | 4/1999 | Barnhart |
| 5,897,491 A | 4/1999 | Kastenbauer et al. |
| 5,924,175 A | 7/1999 | Lippitt |
| 5,943,056 A | 8/1999 | Sato |
| 5,989,230 A | 11/1999 | Frassica |
| 6,071,281 A | 6/2000 | Burnside et al. |
| 6,093,157 A | 7/2000 | Chandrasekaran |
| 6,110,171 A | 8/2000 | Rydell |
| 6,120,476 A | 9/2000 | Fung et al. |
| 6,120,498 A | 9/2000 | Jani et al. |
| 6,156,030 A | 12/2000 | Neev |
| 6,174,318 B1 | 1/2001 | Bates et al. |
| 6,183,435 B1 | 2/2001 | Bumbalough et al. |
| 6,206,903 B1 | 3/2001 | Ramans |
| 6,236,906 B1 | 5/2001 | Muller |
| 6,322,557 B1 | 11/2001 | Nikolaevich |
| 6,375,635 B1 | 4/2002 | Moutafis |
| 6,394,998 B1 | 5/2002 | Wallace et al. |
| 6,405,078 B1 | 6/2002 | Moaddeb et al. |
| 6,440,061 B1 | 8/2002 | Wenner et al. |
| 6,459,926 B1 * | 10/2002 | Nowlin .................. A61B 34/30 600/102 |
| 6,508,823 B1 | 1/2003 | Gonon |
| 6,522,906 B1 | 2/2003 | Salisbury et al. |
| 6,577,891 B1 | 6/2003 | Jaross et al. |
| 6,676,668 B2 | 1/2004 | Mercereau et al. |
| 6,685,698 B2 | 2/2004 | Morley et al. |
| 6,706,050 B1 | 3/2004 | Giannadakis |
| 7,282,055 B2 | 10/2007 | Tsuruta |
| 7,559,934 B2 | 7/2009 | Teague et al. |
| 7,736,356 B2 | 6/2010 | Cooper et al. |
| 7,963,911 B2 | 6/2011 | Turliuc |
| 7,987,046 B1 | 7/2011 | Peterman |
| 8,002,713 B2 | 8/2011 | Heske |
| 8,004,229 B2 * | 8/2011 | Nowlin .................. A61B 90/37 318/568.2 |
| 8,021,326 B2 | 9/2011 | Moll et al. |
| 8,038,598 B2 | 10/2011 | Khachi |
| 8,092,397 B2 | 1/2012 | Wallace et al. |
| 8,187,173 B2 | 5/2012 | Miyoshi |
| 8,257,303 B2 | 9/2012 | Moll et al. |
| 8,480,595 B2 | 7/2013 | Speeg |
| 8,523,762 B2 | 9/2013 | Miyamoto et al. |
| 8,540,748 B2 | 9/2013 | Murphy et al. |
| 8,541,970 B2 | 9/2013 | Nowlin |
| 8,652,030 B2 | 2/2014 | Matsuura et al. |
| 8,749,189 B2 | 6/2014 | Nowlin et al. |
| 8,749,190 B2 | 6/2014 | Nowlin et al. |
| 8,786,241 B2 | 7/2014 | Nowlin et al. |
| 8,820,603 B2 | 9/2014 | Shelton et al. |
| 8,821,480 B2 | 9/2014 | Burbank |
| 8,823,308 B2 | 9/2014 | Nowlin et al. |
| 8,882,660 B2 | 11/2014 | Phee et al. |
| 8,945,163 B2 | 2/2015 | Voegele et al. |
| 8,956,280 B2 | 2/2015 | Eversull et al. |
| 9,179,979 B2 | 11/2015 | Jinno |
| 9,259,282 B2 | 2/2016 | Azizian |
| 9,296,104 B2 | 3/2016 | Swarup et al. |
| 9,345,456 B2 | 5/2016 | Tsonton et al. |
| 9,345,544 B2 | 5/2016 | Hourtash et al. |
| 9,375,284 B2 | 6/2016 | Hourtash |
| 9,415,510 B2 | 8/2016 | Hourtash et al. |
| 9,460,536 B2 | 10/2016 | Hasegawa et al. |
| 9,480,534 B2 | 11/2016 | Bowling |
| 9,504,604 B2 | 11/2016 | Alvarez |
| 9,510,911 B2 | 12/2016 | Hourtash |
| 9,517,106 B2 | 12/2016 | Hourtash et al. |
| 9,561,083 B2 | 2/2017 | Yu et al. |
| 9,566,125 B2 | 2/2017 | Bowling |
| 9,592,042 B2 | 3/2017 | Titus |
| 9,597,152 B2 | 3/2017 | Schaeffer |
| 9,622,827 B2 | 4/2017 | Yu et al. |
| 9,636,184 B2 | 5/2017 | Lee et al. |
| 9,668,768 B2 | 6/2017 | Piron et al. |
| 9,675,422 B2 | 6/2017 | Hourtash et al. |
| 9,687,310 B2 | 6/2017 | Nowlin et al. |
| 9,713,509 B2 | 7/2017 | Schuh et al. |
| 9,717,563 B2 | 8/2017 | Tognaccini |
| 9,727,963 B2 | 8/2017 | Mintz et al. |
| 9,730,757 B2 | 8/2017 | Brudniok |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,782,229 B2 | 10/2017 | Crawford |
| 9,788,910 B2 | 10/2017 | Schuh |
| 9,844,412 B2 | 12/2017 | Bogusky et al. |
| 9,867,635 B2 | 1/2018 | Alvarez et al. |
| 9,918,681 B2 | 3/2018 | Wallace et al. |
| 9,931,025 B1 | 4/2018 | Graetzel et al. |
| 9,943,962 B2 | 4/2018 | Sattler et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,029,367 B2 | 7/2018 | Hourtash |
| 10,071,479 B2 | 9/2018 | Swarup et al. |
| 10,080,576 B2 | 9/2018 | Romo et al. |
| 10,117,713 B2 | 11/2018 | Moctezuma de la Barrera |
| 10,123,844 B2 | 11/2018 | Nowlin et al. |
| 10,130,429 B1 | 11/2018 | Weir |

(56) References Cited

U.S. PATENT DOCUMENTS

| | | | |
|---|---|---|---|
| 10,136,949 B2 | 11/2018 | Felder et al. | |
| 10,136,959 B2 | 11/2018 | Mintz et al. | |
| 10,145,747 B1 | 12/2018 | Lin et al. | |
| 10,149,720 B2 | 12/2018 | Romo | |
| 10,154,822 B2 | 12/2018 | Henderson | |
| 10,159,532 B1 | 12/2018 | Ummalaneni et al. | |
| 10,159,533 B2 | 12/2018 | Moll et al. | |
| 10,169,875 B2 | 1/2019 | Mintz et al. | |
| 10,194,998 B2 | 2/2019 | Nowlin et al. | |
| 10,219,868 B2 | 3/2019 | Weir | |
| 10,219,874 B2 | 3/2019 | Yu et al. | |
| 10,231,793 B2 | 3/2019 | Romo | |
| 10,231,867 B2 | 3/2019 | Alvarez et al. | |
| 10,244,926 B2 | 4/2019 | Noonan et al. | |
| 10,285,574 B2 | 5/2019 | Landey et al. | |
| 10,299,870 B2 | 5/2019 | Connolly et al. | |
| 10,314,463 B2 | 6/2019 | Agrawal et al. | |
| 10,314,661 B2 | 6/2019 | Bowling | |
| 10,327,855 B2 | 6/2019 | Hourtash et al. | |
| 10,350,017 B2 | 7/2019 | Bowling | |
| 10,350,390 B2 | 7/2019 | Moll et al. | |
| 10,383,765 B2 | 8/2019 | Alvarez et al. | |
| 10,398,518 B2 | 9/2019 | Yu et al. | |
| 10,405,939 B2 | 9/2019 | Romo et al. | |
| 10,405,940 B2 | 9/2019 | Romo | |
| 10,426,559 B2 | 10/2019 | Graetzel et al. | |
| 10,426,661 B2 | 10/2019 | Kintz | |
| 10,434,660 B2 | 10/2019 | Meyer et al. | |
| 10,463,440 B2 | 11/2019 | Bowling | |
| 10,464,209 B2 | 11/2019 | Ho et al. | |
| 10,470,830 B2 | 11/2019 | Hill | |
| 10,482,599 B2 | 11/2019 | Mintz et al. | |
| 10,493,241 B2 | 12/2019 | Jiang | |
| 10,500,001 B2 | 12/2019 | Yu et al. | |
| 10,512,514 B2 | 12/2019 | Nowlin et al. | |
| 10,517,692 B2 | 12/2019 | Eyre et al. | |
| 10,524,866 B2 | 1/2020 | Srinivasan | |
| 10,539,478 B2 | 1/2020 | Lin | |
| 10,543,048 B2 | 1/2020 | Noonan et al. | |
| 10,555,778 B2 | 2/2020 | Ummalaneni et al. | |
| 10,631,949 B2 | 4/2020 | Schuh et al. | |
| 10,639,108 B2 | 5/2020 | Romo et al. | |
| 10,639,109 B2 | 5/2020 | Bovay et al. | |
| 10,639,114 B2 | 5/2020 | Schuh | |
| 10,646,291 B2 | 5/2020 | Turner | |
| 10,667,871 B2 | 6/2020 | Romo et al. | |
| 10,667,875 B2 | 6/2020 | DeFonzo | |
| 10,682,189 B2 | 6/2020 | Schuh et al. | |
| 10,702,348 B2 | 7/2020 | Moll et al. | |
| 10,716,461 B2 | 7/2020 | Jenkins | |
| 10,743,751 B2 | 8/2020 | Landey et al. | |
| 10,744,035 B2 | 8/2020 | Alvarez et al. | |
| 10,751,140 B2 | 8/2020 | Wallace et al. | |
| 10,765,303 B2 | 9/2020 | Graetzel et al. | |
| 10,765,487 B2 | 9/2020 | Ho | |
| 10,779,898 B2 | 9/2020 | Hill | |
| 10,786,329 B2 | 9/2020 | Schuh et al. | |
| 10,786,432 B2 | 10/2020 | Mintz et al. | |
| 10,792,464 B2 | 10/2020 | Romo et al. | |
| 10,792,466 B2 | 10/2020 | Landey et al. | |
| 10,813,539 B2 | 10/2020 | Graetzel et al. | |
| 10,814,101 B2 | 10/2020 | Jiang | |
| 10,820,947 B2 | 11/2020 | Julian | |
| 10,820,954 B2 | 11/2020 | Marsot et al. | |
| 10,827,913 B2 | 11/2020 | Ummalaneni et al. | |
| 10,828,118 B2 | 11/2020 | Schuh et al. | |
| 10,835,153 B2 | 11/2020 | Rafii-Tari et al. | |
| 10,850,013 B2 | 12/2020 | Hsu | |
| 2002/0019644 A1 | 2/2002 | Hastings | |
| 2002/0082612 A1 | 6/2002 | Moll et al. | |
| 2002/0111608 A1 | 8/2002 | Baerveldt | |
| 2002/0111621 A1 | 8/2002 | Wallace et al. | |
| 2003/0004455 A1 | 1/2003 | Kadziauskas | |
| 2003/0040681 A1 | 2/2003 | Ng et al. | |
| 2003/0065358 A1 | 4/2003 | Frecker | |
| 2003/0100892 A1 | 5/2003 | Morley et al. | |
| 2003/0109780 A1* | 6/2003 | Coste-Maniere | G06T 7/0012 600/407 |
| 2003/0109877 A1 | 6/2003 | Morley | |
| 2003/0109889 A1 | 6/2003 | Mercereau | |
| 2003/0158545 A1 | 8/2003 | Hovda et al. | |
| 2003/0181809 A1 | 9/2003 | Hall et al. | |
| 2003/0208189 A1 | 11/2003 | Payman | |
| 2004/0143253 A1 | 7/2004 | Vanney | |
| 2004/0153093 A1 | 8/2004 | Donovan | |
| 2004/0158261 A1 | 8/2004 | Vu | |
| 2004/0176751 A1 | 9/2004 | Weitzner et al. | |
| 2004/0186349 A1 | 9/2004 | Ewers | |
| 2004/0193146 A1 | 9/2004 | Lee et al. | |
| 2004/0210116 A1 | 10/2004 | Nakao | |
| 2004/0253079 A1 | 12/2004 | Sanchez | |
| 2005/0033270 A1 | 2/2005 | Ramans et al. | |
| 2005/0054900 A1 | 3/2005 | Mawn | |
| 2005/0159645 A1 | 7/2005 | Bertolero | |
| 2005/0240178 A1 | 10/2005 | Morley et al. | |
| 2005/0261705 A1 | 11/2005 | Gist | |
| 2006/0015133 A1 | 1/2006 | Grayzel | |
| 2006/0058617 A1 | 3/2006 | Sano et al. | |
| 2006/0058813 A1 | 3/2006 | Teague | |
| 2006/0116693 A1 | 6/2006 | Weisenburgh | |
| 2006/0135963 A1 | 6/2006 | Kick | |
| 2006/0156875 A1 | 7/2006 | McRury et al. | |
| 2006/0161137 A1 | 7/2006 | Orban et al. | |
| 2006/0178556 A1 | 8/2006 | Hasser et al. | |
| 2006/0189891 A1 | 8/2006 | Waxman et al. | |
| 2007/0016164 A1 | 1/2007 | Dudney et al. | |
| 2007/0027443 A1 | 2/2007 | Rose | |
| 2007/0027534 A1 | 2/2007 | Bergheim | |
| 2007/0032906 A1 | 2/2007 | Sutherland et al. | |
| 2007/0106304 A1 | 5/2007 | Hammack | |
| 2007/0123855 A1 | 5/2007 | Morley et al. | |
| 2007/0135803 A1 | 6/2007 | Belson | |
| 2007/0208375 A1 | 9/2007 | Nishizawa | |
| 2007/0213668 A1 | 9/2007 | Spitz | |
| 2007/0239178 A1 | 10/2007 | Weitzner et al. | |
| 2007/0250111 A1 | 10/2007 | Lu | |
| 2007/0299427 A1 | 12/2007 | Yeung et al. | |
| 2008/0015566 A1 | 1/2008 | Livneh | |
| 2008/0021440 A1 | 1/2008 | Solomon | |
| 2008/0033467 A1 | 2/2008 | Miyamoto et al. | |
| 2008/0045981 A1 | 2/2008 | Margolin et al. | |
| 2008/0046122 A1 | 2/2008 | Manzo et al. | |
| 2008/0065111 A1 | 3/2008 | Blumenkranz et al. | |
| 2008/0065112 A1 | 3/2008 | Tovey et al. | |
| 2008/0125698 A1 | 5/2008 | Gerg et al. | |
| 2008/0147089 A1 | 6/2008 | Loh | |
| 2008/0187101 A1 | 8/2008 | Gertner | |
| 2008/0196533 A1 | 8/2008 | Bergamasco | |
| 2008/0228104 A1 | 9/2008 | Uber et al. | |
| 2009/0005768 A1 | 1/2009 | Sharareh | |
| 2009/0012507 A1 | 1/2009 | Culbertson et al. | |
| 2009/0030446 A1 | 1/2009 | Measamer | |
| 2009/0036900 A1 | 2/2009 | Moll | |
| 2009/0043305 A1 | 2/2009 | Brodbeck | |
| 2009/0048611 A1 | 2/2009 | Funda | |
| 2009/0082634 A1 | 3/2009 | Kathrani et al. | |
| 2009/0088774 A1 | 4/2009 | Swarup et al. | |
| 2009/0105723 A1 | 4/2009 | Dillinger | |
| 2009/0131885 A1 | 5/2009 | Akahoshi | |
| 2009/0161827 A1 | 6/2009 | Gertner et al. | |
| 2009/0192524 A1 | 7/2009 | Itkowitz | |
| 2009/0227998 A1 | 9/2009 | Aljuri | |
| 2009/0248038 A1* | 10/2009 | Blumenkranz | A61B 34/30 606/130 |
| 2009/0248041 A1 | 10/2009 | Williams et al. | |
| 2009/0248043 A1 | 10/2009 | Tierney et al. | |
| 2009/0264878 A1 | 10/2009 | Carmel et al. | |
| 2009/0270760 A1 | 10/2009 | Leimbach et al. | |
| 2009/0287188 A1 | 11/2009 | Golden et al. | |
| 2009/0299352 A1 | 12/2009 | Zerfas | |
| 2009/0312773 A1 | 12/2009 | Cabrera et al. | |
| 2009/0326318 A1 | 12/2009 | Tognaccini | |
| 2010/0004642 A1 | 1/2010 | Lumpkin | |
| 2010/0010504 A1 | 1/2010 | Simaan et al. | |

(56) References Cited

U.S. PATENT DOCUMENTS

| | | |
|---|---|---|
| 2010/0011900 A1 | 1/2010 | Burbank |
| 2010/0011901 A1 | 1/2010 | Burbank |
| 2010/0016852 A1 | 1/2010 | Manzo et al. |
| 2010/0016853 A1 | 1/2010 | Burbank |
| 2010/0081965 A1 | 4/2010 | Mugan et al. |
| 2010/0082017 A1 | 4/2010 | Zickler |
| 2010/0100045 A1 | 4/2010 | Pravongviengkham et al. |
| 2010/0179632 A1 | 7/2010 | Bruszewski et al. |
| 2010/0204605 A1 | 8/2010 | Blakley |
| 2010/0204646 A1 | 8/2010 | Plicchi et al. |
| 2010/0217235 A1 | 8/2010 | Thorstenson |
| 2010/0225209 A1 | 9/2010 | Goldberg |
| 2010/0228249 A1 | 9/2010 | Mohr |
| 2010/0234857 A1 | 9/2010 | Itkowitz |
| 2010/0268211 A1 | 10/2010 | Manwaring et al. |
| 2010/0286712 A1 | 11/2010 | Won et al. |
| 2010/0312141 A1 | 12/2010 | Keast et al. |
| 2010/0331858 A1 | 12/2010 | Simaan et al. |
| 2011/0015483 A1 | 1/2011 | Barbagli |
| 2011/0028790 A1 | 2/2011 | Farr et al. |
| 2011/0029133 A1* | 2/2011 | Okazaki ............... B25J 9/142 700/258 |
| 2011/0071541 A1 | 3/2011 | Prisco et al. |
| 2011/0071543 A1 | 3/2011 | Prisco et al. |
| 2011/0106146 A1 | 5/2011 | Jeong |
| 2011/0125165 A1 | 5/2011 | Simaan et al. |
| 2011/0152880 A1 | 6/2011 | Alvarez et al. |
| 2011/0160713 A1 | 6/2011 | Neuberger |
| 2011/0160745 A1 | 6/2011 | Fielding |
| 2011/0167611 A1 | 7/2011 | Williams |
| 2011/0184558 A1 | 7/2011 | Jacob |
| 2011/0208211 A1 | 8/2011 | Whitfield et al. |
| 2011/0213362 A1 | 9/2011 | Cunningham et al. |
| 2011/0224660 A1 | 9/2011 | Neuberger et al. |
| 2011/0238064 A1 | 9/2011 | Williams |
| 2011/0257641 A1 | 10/2011 | Hastings et al. |
| 2011/0264112 A1 | 10/2011 | Nowlin et al. |
| 2011/0276085 A1 | 11/2011 | Krzyzanowski |
| 2011/0277775 A1 | 11/2011 | Holop et al. |
| 2011/0313343 A1 | 12/2011 | Milutinovic et al. |
| 2012/0048759 A1 | 3/2012 | Disch et al. |
| 2012/0069167 A1 | 3/2012 | Liu et al. |
| 2012/0138586 A1 | 6/2012 | Webster et al. |
| 2012/0138660 A1 | 6/2012 | Shelton, IV et al. |
| 2012/0209315 A1 | 8/2012 | Amat |
| 2012/0232342 A1 | 9/2012 | Reydel |
| 2012/0253277 A1 | 10/2012 | Tah et al. |
| 2012/0253332 A1 | 10/2012 | Moll |
| 2012/0259320 A1 | 10/2012 | Loesel et al. |
| 2012/0283747 A1 | 11/2012 | Popovic |
| 2012/0296318 A1 | 11/2012 | Wellhofer et al. |
| 2012/0302869 A1 | 11/2012 | Koyrakh |
| 2013/0006144 A1 | 1/2013 | Clancy |
| 2013/0035537 A1 | 2/2013 | Wallace et al. |
| 2013/0053877 A1 | 2/2013 | BenMaamer |
| 2013/0066136 A1 | 3/2013 | Palese et al. |
| 2013/0085442 A1 | 4/2013 | Shtul et al. |
| 2013/0085486 A1 | 4/2013 | Boutoussov et al. |
| 2013/0096422 A1 | 4/2013 | Boctor |
| 2013/0096574 A1 | 4/2013 | Kang et al. |
| 2013/0110042 A1 | 5/2013 | Humphreys |
| 2013/0110107 A1 | 5/2013 | Smith et al. |
| 2013/0116716 A1 | 5/2013 | Bahls et al. |
| 2013/0144274 A1 | 6/2013 | Stefanchik et al. |
| 2013/0144395 A1 | 6/2013 | Stefanchik |
| 2013/0190796 A1 | 7/2013 | Tilson et al. |
| 2013/0225997 A1 | 8/2013 | Dillard et al. |
| 2013/0226161 A1 | 8/2013 | Hickenbotham |
| 2013/0233908 A1 | 9/2013 | Knodel |
| 2013/0253267 A1 | 9/2013 | Collins |
| 2013/0303876 A1 | 11/2013 | Gelfand et al. |
| 2013/0310819 A1 | 11/2013 | Neuberger et al. |
| 2013/0317519 A1 | 11/2013 | Romo et al. |
| 2013/0334281 A1 | 12/2013 | Williams |
| 2013/0345686 A1 | 12/2013 | Brown |
| 2014/0005681 A1 | 1/2014 | Gee et al. |
| 2014/0039517 A1 | 2/2014 | Bowling |
| 2014/0039681 A1 | 2/2014 | Bowling |
| 2014/0046308 A1 | 2/2014 | Bischoff |
| 2014/0051049 A1 | 2/2014 | Jarc |
| 2014/0051985 A1 | 2/2014 | Fan et al. |
| 2014/0058365 A1 | 2/2014 | Bille |
| 2014/0058404 A1 | 2/2014 | Hammack |
| 2014/0058428 A1 | 2/2014 | Christopher |
| 2014/0100445 A1 | 4/2014 | Stenzel |
| 2014/0142591 A1 | 5/2014 | Alvarez et al. |
| 2014/0163318 A1 | 6/2014 | Swanstrom |
| 2014/0163736 A1 | 6/2014 | Azizian |
| 2014/0194859 A1 | 7/2014 | Ianchulev |
| 2014/0194905 A1 | 7/2014 | Kappel |
| 2014/0222207 A1 | 8/2014 | Bowling |
| 2014/0243801 A1 | 8/2014 | Fanelli et al. |
| 2014/0243849 A1 | 8/2014 | Saglam et al. |
| 2014/0246473 A1 | 9/2014 | Auld |
| 2014/0257333 A1 | 9/2014 | Blumenkranz |
| 2014/0275956 A1 | 9/2014 | Fan |
| 2014/0276723 A1 | 9/2014 | Parihar |
| 2014/0276956 A1 | 9/2014 | Crainich |
| 2014/0309655 A1 | 10/2014 | Gal et al. |
| 2014/0316203 A1 | 10/2014 | Carroux et al. |
| 2014/0357984 A1 | 12/2014 | Wallace et al. |
| 2015/0025549 A1 | 1/2015 | Kilroy et al. |
| 2015/0045675 A1 | 2/2015 | Chernomorsky |
| 2015/0073439 A1 | 3/2015 | Dannaher |
| 2015/0080879 A1 | 3/2015 | Trees |
| 2015/0088161 A1 | 3/2015 | Hata |
| 2015/0127045 A1 | 5/2015 | Prestel |
| 2015/0133960 A1 | 5/2015 | Lohmeier |
| 2015/0150635 A1 | 6/2015 | Kilroy et al. |
| 2015/0164522 A1 | 6/2015 | Budiman |
| 2015/0190204 A1 | 7/2015 | Popovi |
| 2015/0201917 A1 | 7/2015 | Snow |
| 2015/0202085 A1 | 7/2015 | Lemonis |
| 2015/0223832 A1 | 8/2015 | Swaney |
| 2015/0297299 A1 | 10/2015 | Yeung |
| 2015/0305650 A1 | 10/2015 | Hunter |
| 2015/0314110 A1 | 11/2015 | Park |
| 2015/0366629 A1 | 12/2015 | Bowling |
| 2015/0374446 A1 | 12/2015 | Malackowski |
| 2016/0022289 A1 | 1/2016 | Wan |
| 2016/0022466 A1 | 1/2016 | Pedtke |
| 2016/0030073 A1 | 2/2016 | Lsakov |
| 2016/0045208 A1 | 2/2016 | Ciulla |
| 2016/0051318 A1 | 2/2016 | Manzo et al. |
| 2016/0066935 A1 | 3/2016 | Nguyen et al. |
| 2016/0158490 A1 | 6/2016 | Leeflang |
| 2016/0183841 A1 | 6/2016 | Duindarn et al. |
| 2016/0199984 A1 | 7/2016 | Lohmeier et al. |
| 2016/0235495 A1 | 8/2016 | Wallace et al. |
| 2016/0242858 A1 | 8/2016 | Moctezuma de la Barrera |
| 2016/0249932 A1 | 9/2016 | Rogers et al. |
| 2016/0270865 A1 | 9/2016 | Landey et al. |
| 2016/0287279 A1 | 10/2016 | Bovay et al. |
| 2016/0302871 A1 | 10/2016 | Gregerson et al. |
| 2016/0303743 A1 | 10/2016 | Rockrohr |
| 2016/0310146 A1 | 10/2016 | Levy et al. |
| 2016/0331358 A1 | 11/2016 | Gordon |
| 2016/0367324 A1 | 12/2016 | Sato et al. |
| 2017/0000577 A1 | 1/2017 | Bowling |
| 2017/0007337 A1 | 1/2017 | Dan |
| 2017/0020615 A1 | 1/2017 | Koenig et al. |
| 2017/0049471 A1 | 2/2017 | Gaffney et al. |
| 2017/0055995 A1 | 3/2017 | Weier |
| 2017/0056117 A1* | 3/2017 | Hourtash ............... B25J 9/1676 |
| 2017/0065227 A1 | 3/2017 | Marrs |
| 2017/0071456 A1 | 3/2017 | Ratnakar |
| 2017/0071584 A1 | 3/2017 | Suigetsu et al. |
| 2017/0086934 A1 | 3/2017 | Devengenzo et al. |
| 2017/0095234 A1 | 4/2017 | Prisco et al. |
| 2017/0095295 A1 | 4/2017 | Overmyer |
| 2017/0095299 A1 | 4/2017 | Hendrick |
| 2017/0135706 A1 | 5/2017 | Frey |
| 2017/0135710 A1 | 5/2017 | Hasegawa et al. |
| 2017/0135833 A1 | 5/2017 | Syed |

(56) References Cited

U.S. PATENT DOCUMENTS

| | | |
|---|---|---|
| 2017/0143442 A1 | 5/2017 | Tesar |
| 2017/0151416 A1 | 6/2017 | Kutikov |
| 2017/0165009 A1 | 6/2017 | Chaplin et al. |
| 2017/0172553 A1 | 6/2017 | Chaplin |
| 2017/0172680 A1 | 6/2017 | Bowling |
| 2017/0189118 A1 | 7/2017 | Chopra et al. |
| 2017/0189131 A1 | 7/2017 | Weir |
| 2017/0202627 A1 | 7/2017 | Sramek et al. |
| 2017/0209073 A1 | 7/2017 | Sramek et al. |
| 2017/0252096 A1 | 9/2017 | Felder |
| 2017/0258534 A1 | 9/2017 | Hourtash et al. |
| 2017/0265923 A1 | 9/2017 | Privitera |
| 2017/0265954 A1 | 9/2017 | Burbank |
| 2017/0290631 A1 | 10/2017 | Lee et al. |
| 2017/0319289 A1 | 11/2017 | Neff et al. |
| 2017/0333145 A1 | 11/2017 | Griffiths |
| 2017/0333147 A1 | 11/2017 | Bernstein |
| 2017/0334070 A1 * | 11/2017 | Bordegnoni ......... B25J 19/0075 |
| 2018/0000563 A1 | 1/2018 | Shanjani et al. |
| 2018/0025666 A1 | 1/2018 | Ho et al. |
| 2018/0049824 A1 | 2/2018 | Harris |
| 2018/0079090 A1 | 3/2018 | Koenig |
| 2018/0080841 A1 | 3/2018 | Cordoba |
| 2018/0098817 A1 | 4/2018 | Nichogi et al. |
| 2018/0140371 A1 | 5/2018 | Hares et al. |
| 2018/0161115 A1 * | 6/2018 | Farritor ................. B25J 9/1602 |
| 2018/0193049 A1 | 7/2018 | Heck et al. |
| 2018/0206931 A1 | 7/2018 | Scheib |
| 2018/0221038 A1 | 8/2018 | Noonan et al. |
| 2018/0221039 A1 | 8/2018 | Shah |
| 2018/0250085 A1 | 9/2018 | Simi |
| 2018/0279852 A1 | 10/2018 | Rafii-Tari et al. |
| 2018/0289431 A1 | 10/2018 | Draper et al. |
| 2018/0296285 A1 | 10/2018 | Simi et al. |
| 2018/0325499 A1 | 11/2018 | Landey et al. |
| 2018/0338799 A1 | 11/2018 | Hladio et al. |
| 2018/0360435 A1 | 12/2018 | Romo |
| 2018/0368920 A1 | 12/2018 | Ummalaneni |
| 2019/0000559 A1 | 1/2019 | Berman et al. |
| 2019/0000560 A1 | 1/2019 | Berman et al. |
| 2019/0000576 A1 | 1/2019 | Mintz et al. |
| 2019/0015166 A1 | 1/2019 | Mahoney |
| 2019/0047154 A1 * | 2/2019 | Itkowitz ................ A61B 90/36 |
| 2019/0054620 A1 * | 2/2019 | Griffiths ................ G16H 50/50 |
| 2019/0069962 A1 | 3/2019 | Tabandeh et al. |
| 2019/0099231 A1 | 4/2019 | Bruehwiler |
| 2019/0099232 A1 | 4/2019 | Soto et al. |
| 2019/0110839 A1 | 4/2019 | Rafii-Tari et al. |
| 2019/0117320 A1 | 4/2019 | Shoham et al. |
| 2019/0117324 A1 | 4/2019 | Hibner |
| 2019/0151148 A1 | 5/2019 | Alvarez et al. |
| 2019/0167366 A1 | 6/2019 | Ummalaneni |
| 2019/0175009 A1 | 6/2019 | Mintz |
| 2019/0183585 A1 | 6/2019 | Rafii-Tari et al. |
| 2019/0183587 A1 | 6/2019 | Rafii-Tari et al. |
| 2019/0192249 A1 | 6/2019 | Bowling |
| 2019/0216548 A1 | 7/2019 | Ummalaneni |
| 2019/0216550 A1 | 7/2019 | Eyre |
| 2019/0216576 A1 | 7/2019 | Eyre |
| 2019/0223974 A1 | 7/2019 | Romo |
| 2019/0231460 A1 | 8/2019 | DiMaio |
| 2019/0239890 A1 | 8/2019 | Stokes |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Aarawal et al. |
| 2019/0298460 A1 | 10/2019 | Al-Jadda |
| 2019/0298464 A1 | 10/2019 | Abbott |
| 2019/0298465 A1 | 10/2019 | Chin |
| 2019/0298469 A1 | 10/2019 | Ramstad et al. |
| 2019/0314616 A1 | 10/2019 | Moll et al. |
| 2019/0336238 A1 | 11/2019 | Yu |
| 2019/0365201 A1 | 12/2019 | Noonan et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0375383 A1 | 12/2019 | Alvarez |
| 2019/0380787 A1 | 12/2019 | Ye |
| 2019/0380797 A1 | 12/2019 | Yu |
| 2020/0000533 A1 | 1/2020 | Schuh |
| 2020/0030046 A1 | 1/2020 | Bowling |
| 2020/0038123 A1 | 2/2020 | Graetzel |
| 2020/0039086 A1 | 2/2020 | Meyer |
| 2020/0046434 A1 | 2/2020 | Graetzel |
| 2020/0060516 A1 | 2/2020 | Baez |
| 2020/0085516 A1 | 3/2020 | DeFonzo |
| 2020/0093549 A1 | 3/2020 | Chin et al. |
| 2020/0093554 A1 | 3/2020 | Schuh |
| 2020/0100855 A1 | 4/2020 | Leparmentier |
| 2020/0107894 A1 | 4/2020 | Wallace |
| 2020/0121502 A1 | 4/2020 | Kintz |
| 2020/0138531 A1 | 5/2020 | Chaplin |
| 2020/0146769 A1 | 5/2020 | Eyre |
| 2020/0163726 A1 | 5/2020 | Tanner |
| 2020/0170720 A1 | 6/2020 | Ummalaneni |
| 2020/0171660 A1 | 6/2020 | Ho |
| 2020/0188043 A1 | 6/2020 | Yu |
| 2020/0197109 A1 | 6/2020 | Chaplin |
| 2020/0197112 A1 | 6/2020 | Chin |
| 2020/0206472 A1 | 7/2020 | Ma |
| 2020/0217733 A1 | 7/2020 | Lin |
| 2020/0222134 A1 | 7/2020 | Schuh |
| 2020/0237458 A1 | 7/2020 | DeFonzo |
| 2020/0261172 A1 | 8/2020 | Romo |
| 2020/0268459 A1 | 8/2020 | Noonan et al. |
| 2020/0268460 A1 | 8/2020 | Tse |
| 2020/0281787 A1 | 9/2020 | Ruiz |
| 2020/0297437 A1 | 9/2020 | Schuh |
| 2020/0297444 A1 | 9/2020 | Camarillo |
| 2020/0305983 A1 | 10/2020 | Yampolsky |
| 2020/0305989 A1 | 10/2020 | Schuh |
| 2020/0305992 A1 | 10/2020 | Schuh |
| 2020/0315717 A1 | 10/2020 | Bovay |
| 2020/0315723 A1 | 10/2020 | Hassan |
| 2020/0323596 A1 | 10/2020 | Moll |
| 2020/0330167 A1 | 10/2020 | Romo |
| 2020/0345216 A1 | 11/2020 | Jenkins |
| 2020/0352420 A1 | 11/2020 | Graetzel |
| 2020/0360183 A1 | 11/2020 | Alvarez |
| 2020/0367726 A1 | 11/2020 | Landey et al. |
| 2020/0367981 A1 | 11/2020 | Ho et al. |
| 2020/0375678 A1 | 12/2020 | Wallace |
| 2021/0401524 A1 * | 12/2021 | Suresh ................... A61B 34/35 |

FOREIGN PATENT DOCUMENTS

| | | |
|---|---|---|
| CN | 103298414 | 9/2013 |
| CN | 104619281 | 5/2015 |
| CN | 205729413 | 11/2016 |
| CN | 110179541 A * | 8/2019 |
| EP | 0347098 | 2/1996 |
| EP | 1321106 | 6/2003 |
| EP | 1849423 | 10/2007 |
| JP | 2005270464 | 10/2005 |
| KR | 10-2015-0039801 A | 4/2015 |
| WO | WO-06/124390 | 11/2006 |
| WO | 2009/123891 A1 | 10/2009 |
| WO | WO-11/161218 | 12/2011 |
| WO | WO-13/107468 | 7/2013 |
| WO | WO-15/153174 | 10/2015 |
| WO | WO-16/137612 | 9/2016 |
| WO | WO-17/048194 | 3/2017 |
| WO | WO-17/114855 | 7/2017 |
| WO | WO-18/069679 | 4/2018 |
| WO | WO-18/189722 | 10/2018 |
| WO | 2019/074669 A1 | 4/2019 |
| WO | 2020/102776 A1 | 5/2020 |
| WO | WO-2020263520 A1 * | 12/2020 ............. A61B 34/32 |

OTHER PUBLICATIONS

Choi, et al., "A Force/Moment Direction Sensor and Its Application in Intuitive Robot Teaching Task," ICASE: The Institute of Control,

(56) References Cited

OTHER PUBLICATIONS

Automation and Systems Engineers, Korea, Dec. 2001, vol. 3, No. 4, pp. 236-241.

Whitney, "Force Feedback Control of Manipulator Fine Motions," Journal of Dynamic Systems, Measurement and Control, Jun. 1977, pp. 91-97.

Aghakhani et al., May 6, 2013, Task control with remote center of motion constraint for minimally invasive robotic surgery, 2013 IEEE International Conference on Robotics and Automation, pp. 5807-5812.

Darwiche, 2015, Operative technique and early experience for robotic assisted laparoscopic nephroueterectomy (RALNU) using da Vinci XI, SpingerPlus, 4:298.

Hernansanz et al, A multi-robot cooperation strategy for dexterous task oriented teleoperation, 2015, Elsevier, Robotics and Autonomous Systems 68 (205), 156-172 (Year: 2015).

Ramezanifard et al, A Novel Modeling Approach for Collision Avoidance in Robotic Surgery, 2007 Science Publications, American Journal of Applied Sciences 4 (9): 693-699 (Year: 2007).

Sasaki, 2017, Laparoscopic hemicolectomy for a patient with situs inversus totalis: a case report, Int. J. Surg. Case Rep. 41;93-96.

International Preliminary Report on Patentability dated Apr. 7, 2022, issued in International Application No. PCT/IB2020/058715, 14 pages.

PCT International Search Report; PCT/IB2021/055496; Sep. 27, 2021; 6 pages.

PCT Written Opinion of the International Searching Authority; PCT/IB2021/055496; Sep. 27, 2021; 4 pages.

PCT International Preliminary Report on Patentability; PCT/IB2021/055496; Dec. 13, 2022; 5 pages.

European Extended Search Report and Written Opinion dated Jul. 5, 2024, for Application No. 21833194.0, 10 pages.

\* cited by examiner

SYSTEMS AND METHODS FOR DETECTING CONTACT BETWEEN A LINK AND AN EXTERNAL OBJECT

RELATED APPLICATION

This present application is a continuation of U.S. patent application Ser. No. 17/355,151 filed Jun. 22, 2021, now issued as U.S. Pat. No. 11,839,969, which claims the benefit of, and priority to, U.S. Provisional Patent Application No. 63/045,351 filed Jun. 29, 2020, both of which are incorporated herein by reference in their entirety for all purposes.

TECHNOLOGICAL FIELD

The systems and methods disclosed herein are directed to systems and methods for robotic medical systems, and more particularly to detecting contact between a link and an external object.

BACKGROUND

Robotically-enabled medical system may be capable of performing a variety of medical procedures, including both minimally invasive, such as laparoscopy, and non-invasive, such as endoscopy, procedures. Among endoscopic procedures, the system may be capable of performing bronchoscopy, ureteroscopy, gastroscopy, etc.

Such robotic medical systems may include robotic arms configured to control the movement of medical tool(s) during a given medical procedure. In order to achieve a desired pose of a medical tool, a robotic arm may be placed into a pose that may cause the robotic arm to come into contact with another object in the environment. Unintended contact or collisions with such external objects can adversely impact the robotic medical system and/or the external object, and thus it is desirable to detect such collisions.

SUMMARY

The systems, methods and devices of this disclosure each have several innovative aspects, no single one of which is solely responsible for the desirable attributes disclosed herein.

In one aspect, there is provided a robotic system, comprising: a manipulatable link; a rigid shell configured to overlay the manipulatable link; and one or more sensors positioned between the rigid shell and the manipulatable link, the one or more sensors configured to detect contact between the rigid shell and an external object.

In certain implementations, the at least one of the one or more sensors can comprise a beam flexure.

In certain implementations, the beam flexure is configured to engage with an underlying force sensor.

In certain implementations, the manipulatable link comprises a link of a robotic arm.

In certain implementations, the manipulatable link comprises a first link or a second link of the robotic arm.

In certain implementations, at least two or more sensors are located along the proximal link or the distal link of the robotic arm for sensing contact with the respective link.

In certain implementations, the external object comprises a patient, clinician, or inanimate object.

In certain implementations, the rigid shell is suspended over the manipulatable link via the one or more sensors.

In certain implementations, the one or more sensors are further configured to detect a direction of the contact between the rigid shell and the external object.

In certain implementations, the one or more sensors are further configured to measure a magnitude of a force resulting from the contact between the rigid shell and the external object.

In certain implementations, the one or more sensors comprise a first set of one or more sensors and a second set of one or more sensors, the first set of one or more sensor positioned between the rigid shell and the manipulatable link at a proximal end of the manipulatable link, and the second set of one or more sensor positioned between the rigid shell and the manipulatable link at a distal end of the manipulatable link.

In certain implementations, the one or more sensors are further configured to detect a direction of the contact between the rigid shell and the one or more external objects.

In certain implementations, the one or more sensors are further configured to measure a magnitude of a force resulting from the contact between the rigid shell and the one or more external objects.

In certain implementations, the one or more sensors are further configured to measure a torque resulting from the contact between the rigid shell and the one or more external objects.

In certain implementations, the one or more sensors are further configured to measure a direction of relative motion between the rigid shell and the link.

In another aspect, there is provided a sensor assembly for detecting contact with a manipulatable link of a robotic system, the sensor assembly comprising: a beam flexure; an underlying force sensor for detecting contact with the manipulatable link; and a circuit board.

In certain implementations, the beam flexure comprises a first end that is fixed and a second end coupled to the force sensor.

In certain implementations, the beam flexure is engaged with a rigid shell at a point between the first end and the second end.

In certain implementations, the force exerted on the sensor is proportional to the force applied to the point at which the shell engages the flexure.

In certain implementations, the beam flexure is engaged with a rigid shell at a fixed point along the beam flexure.

In certain implementations, a processor is configured to receive an output from the force sensor and generate a force value indicative of a force applied to the rigid shell.

In yet another aspect, there is provided a robotic system, comprising: a manipulatable link; a rigid shell configured to overlay the manipulatable link; and one or more sensors positioned between the rigid shell and the manipulatable link, the one or more sensors configured to detect contact between one or more external objects and the rigid shell in at least two or more directions.

In certain implementations, the one or more sensors are further configured to detect contact between the one or more external objects and the rigid shell in one or more rotational directions.

In certain implementations, at least one of the one or more sensors comprises a beam flexure.

In certain implementations, the beam flexure engages with an underlying micro-force sensor In certain implementations, the manipulatable link comprises a link of a robotic arm.

In certain implementations, the manipulatable link comprises a proximal link or a distal link of the robotic arm.

In certain implementations, at least two or more sensors are located along the proximal link or the distal link of the robotic arm for sensing contact with the respective link.

In certain implementations, the external object comprises a patient, staff or, inanimate object.

In still yet another aspect, there is provided a method of detecting contact between a robotic manipulator and an external object, the method comprising: receiving a signal from one or more sensors positioned between a link of the robotic manipulator and a rigid shell configured to overlay the link, the received signal indicative of the degree of contact between the rigid shell and the one or more sensors; and determining that contact between the robotic manipulator and the external object has occurred in response to the received signal meeting or exceeding a threshold value.

In certain implementations, the method further comprises: detecting a direction of the contact between the rigid shell and the external object based on the signal received from the one or more sensors.

In certain implementations, the method further comprises: measuring a magnitude of a force resulting from the contact between the rigid shell and the external object based on the signal received from the one or more sensors.

In certain implementations, the method further comprises: measuring a torque resulting from the contact between the rigid shell and the external object based on the signal received from the one or more sensors.

In certain implementations, the method further comprises: measuring a direction of relative motion between the rigid shell and the link.

In another aspect, there is provided a robotic arm, comprising: a link; a rigid shell formed over the link; and one or more sensors configured to detect contact between an external object and the rigid shell.

In certain implementations, the external object comprises one or more of: a patient, a clinician, or an inanimate object.

In certain implementations, the one or more sensors are positioned in an interstitial space between the link and the rigid shell.

In certain implementations, the one or more sensors are further configured to measure a magnitude of a force applied to the link.

In certain implementations, the one or more sensors are further configured to measure a direction of a force applied to the link.

In certain implementations, the one or more sensors are further configured to measure a torque applied to the link.

In certain implementations, the one or more sensors comprise a plurality of sensors positioned at different locations of the link.

In certain implementations, the one or more sensors comprise a plurality of circuit board mounted force sensors.

In certain implementations, the one or more sensors comprise a plurality of strain gauges.

In certain implementations, the one or more sensors comprise a plurality of force sensing resistors.

In certain implementations, the one or more sensors comprise a plurality of capacitive sensors.

In certain implementations, the one or more sensors comprise a plurality of sensors that support the rigid shell without being fixed to the rigid shell.

In certain implementations, a given sensor of the one or more sensors comprises a load concentrator configured to control a point at which the rigid shell applies a force to the given sensor.

In certain implementations, a given sensor of the one or more sensors comprises a flexure configured to scale a force applied to the given sensor and isolate the given sensor from shear forces.

In certain implementations, the one or more sensors are further configured to measure a relative position of the rigid shell relative to the link.

In certain implementations, the robotic arm further comprises: a support configured to support the rigid shell relative to the link.

In certain implementations, the support comprises one or more of: a spring, a flexure, or a suspension.

In certain implementations, the one or more sensors are further configured to measure a direction of relative motion between the rigid shell and the link.

In certain implementations, the one or more sensors are further configured to determine a direction of a force applied to the rigid shell.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview.

Aspects of the present disclosure may be integrated into a robotically-enabled medical system capable of performing a variety of medical procedures, including both minimally invasive, such as laparoscopy, and non-invasive, such as endoscopy, procedures. Among endoscopic procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
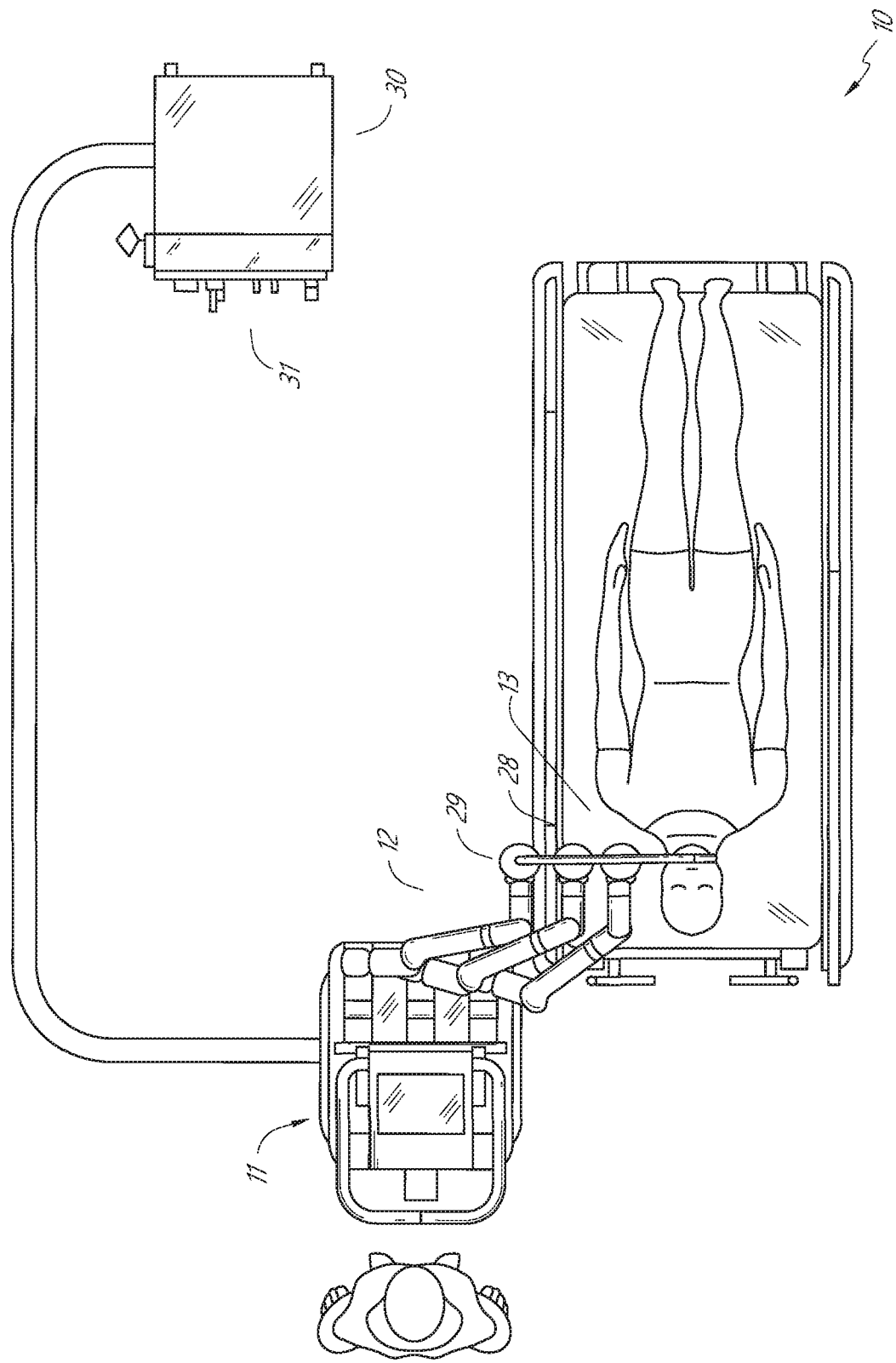
FIG. 1 illustrates an embodiment of a cart-based robotic system arranged for diagnostic and/or therapeutic bronchoscopy.
Figure 2:
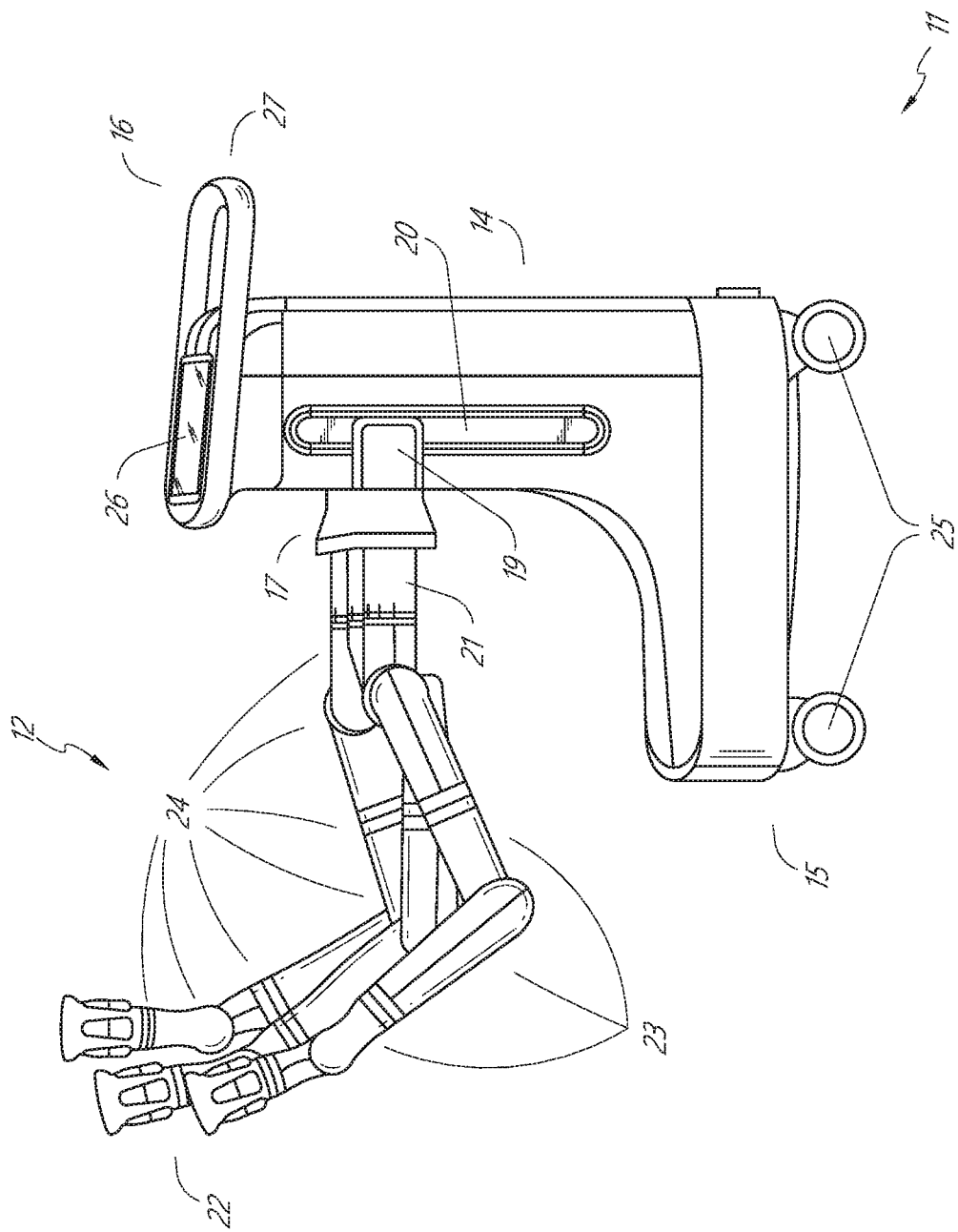
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independently of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of the tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include optoelectronics equipment for detecting, receiving, and processing data received from the optical sensors or cameras throughout the robotic system 10. In combination with the control system, such optoelectronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in the system 10 are generally designed to provide both robotic controls as well as preoperative and real-time information of the procedure, such as navigational and localization information of the endoscope 13. When the console 31 is not the only console available to the physician, it may be used by a second operator, such as a nurse, to monitor the health or vitals of the patient and the operation of the system 10, as well as to provide procedure-specific data, such as navigational and localization information. In other embodiments, the console 31 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart 11, the support for controls, optics, fluidics, and/or navigation may be provided through a separate cable.

FIG. 2 provides a detailed illustration of an embodiment of the cart 11 from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage 17 at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of the robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when the carriage 17 translates towards the spool, while also maintaining a tight seal when the carriage 17 translates away from the spool. The covers may be connected to the carriage 17 using, for example, brackets in the carriage interface 19 to facilitate proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of links 23 that are connected by a series of joints 24, each joint comprising an independent actuator, each actuator comprising an independently controllable motor. Each independently controllable joint represents an independent degree of freedom available to the robotic arm 12. Each of the robotic arms 12 may have seven joints, and thus provide seven degrees of freedom. A multitude of joints result in a multitude of degrees of freedom, allowing for "redundant" degrees of freedom. Having redundant degrees of freedom allows the robotic arms 12 to position their respective end effectors 22 at a specific position, orientation, and trajectory in space using different link positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and robotic arms 12 over the floor. Accordingly, the cart base 15 houses heavier components, such as electronics, motors, power supply, as well as components that either enable movement and/or immobilize the cart 11. For example, the cart base 15 includes rollable wheel-shaped casters 25 that allow for the cart 11 to easily move around the room prior to a procedure. After reaching the appropriate position, the casters 25 may be immobilized using wheel locks to hold the cart 11 in place during the procedure.

Positioned at the vertical end of the column 14, the console 16 allows for both a user interface for receiving user input and a display screen (or a dual-purpose device such as, for example, a touchscreen 26) to provide the physician user with both preoperative and intraoperative data. Potential preoperative data on the touchscreen 26 may include preoperative plans, navigation and mapping data derived from preoperative computerized tomography (CT) scans, and/or notes from preoperative patient interviews. Intraoperative data on display may include optical information provided from the tool, sensor and coordinate information from sensors, as well as vital patient statistics, such as respiration, heart rate, and/or pulse. The console 16 may be positioned and tilted to allow a physician to access the console 16 from the side of the column 14 opposite the carriage 17. From this position, the physician may view the console 16, robotic arms 12, and patient while operating the console 16 from behind the cart 11. As shown, the console 16 also includes a handle 27 to assist with maneuvering and stabilizing the cart 11.

Figure 3:
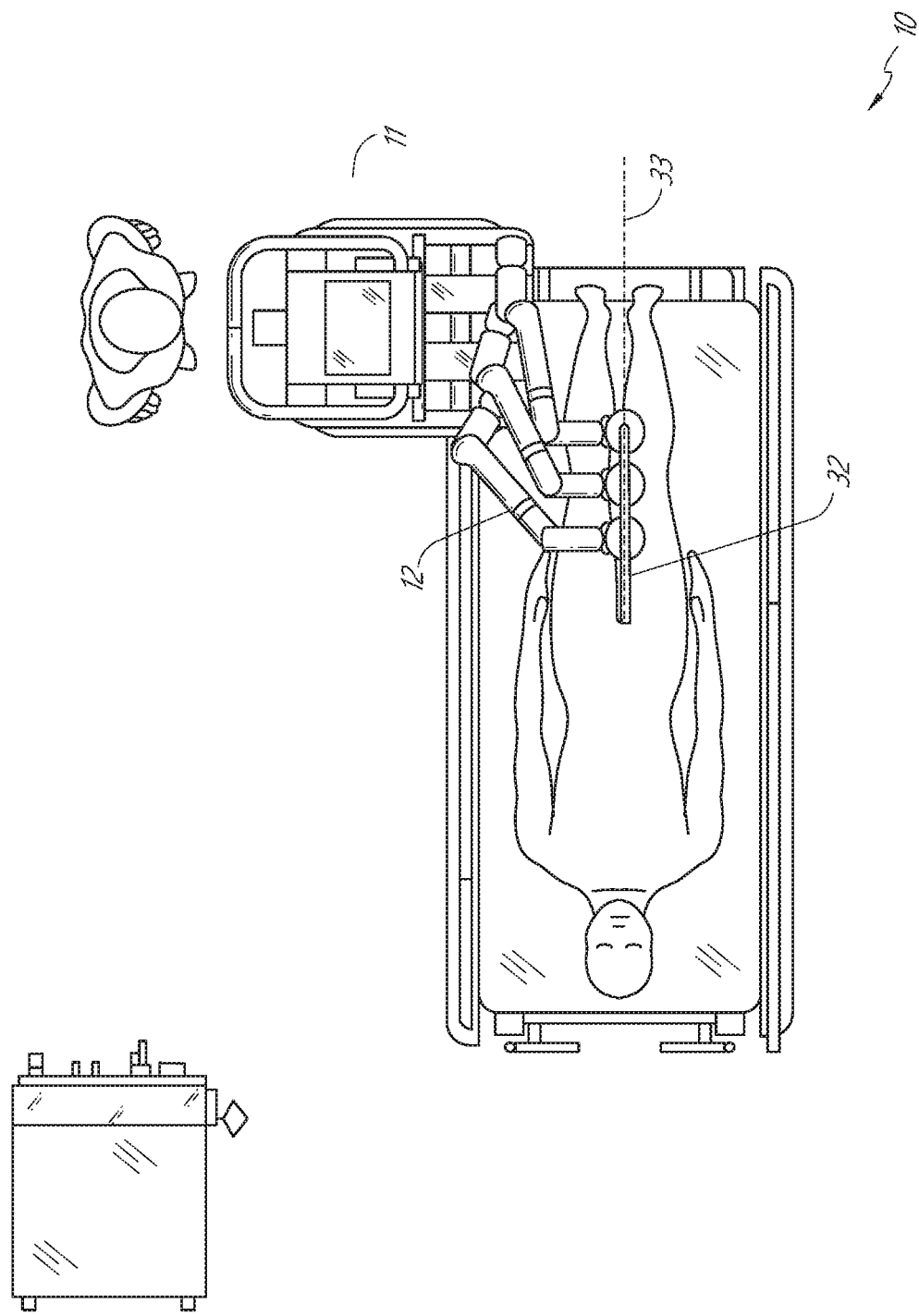
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
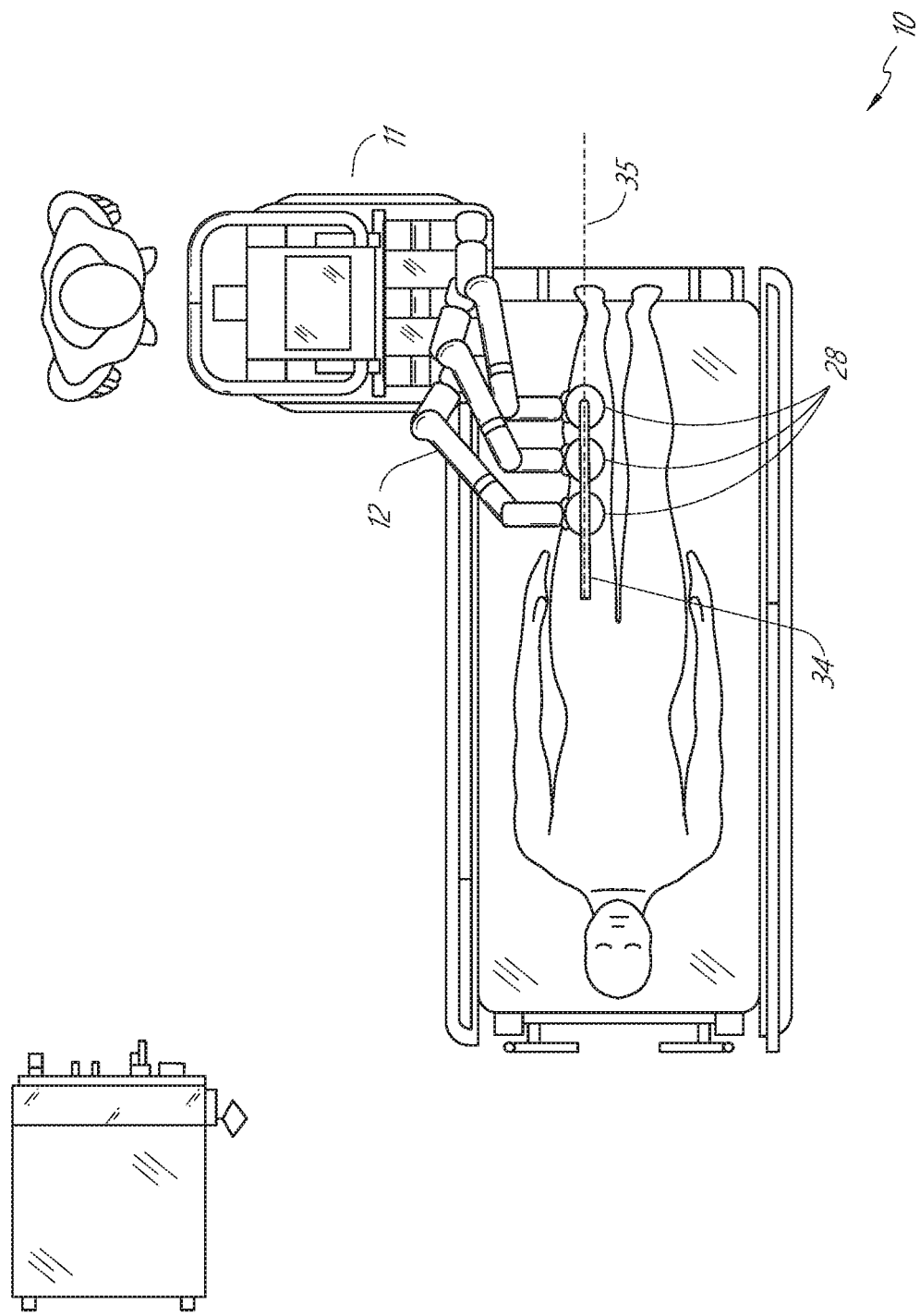
FIG. 4 illustrates an embodiment of the robotic system of FIG. 1 arranged for a vascular procedure.

FIG. 4 illustrates an embodiment of a robotically-enabled system 10 similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
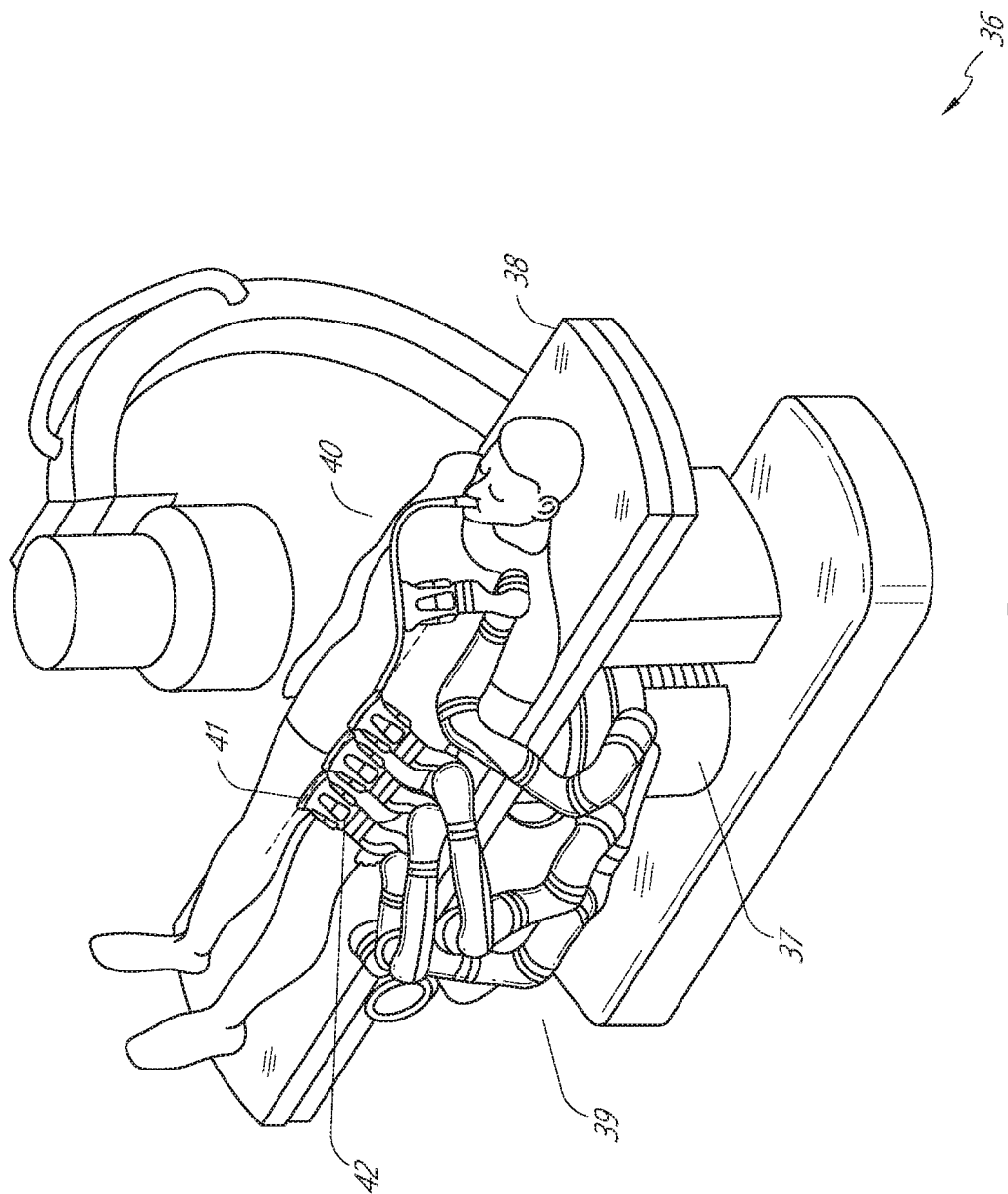
FIG. 5 illustrates an embodiment of a table-based robotic system arranged for a bronchoscopic procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopic procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around the table 38.

Figure 6:
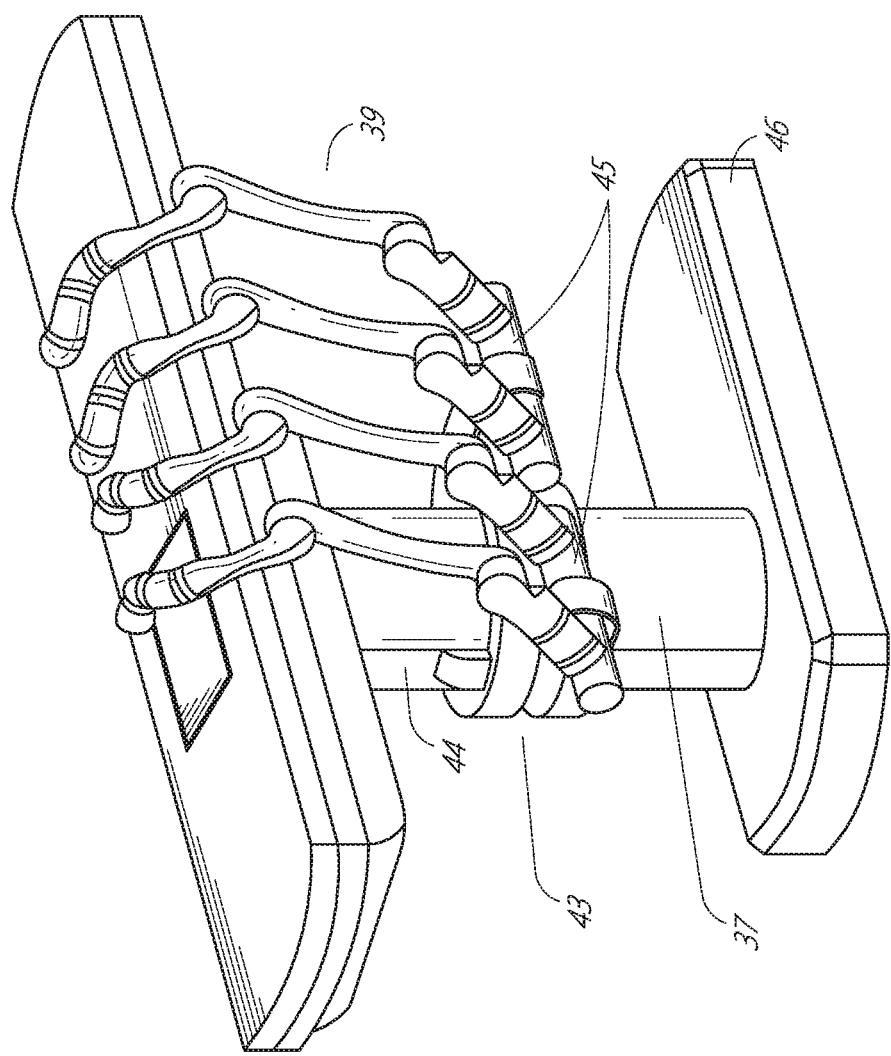
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independently of the other carriages. While the carriages 43 need not surround the column 37 or even be circular, the ring-shape as shown facilitates rotation of the carriages 43 around the column 37 while maintaining structural balance. Rotation and translation of the carriages 43 allows the system 36 to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
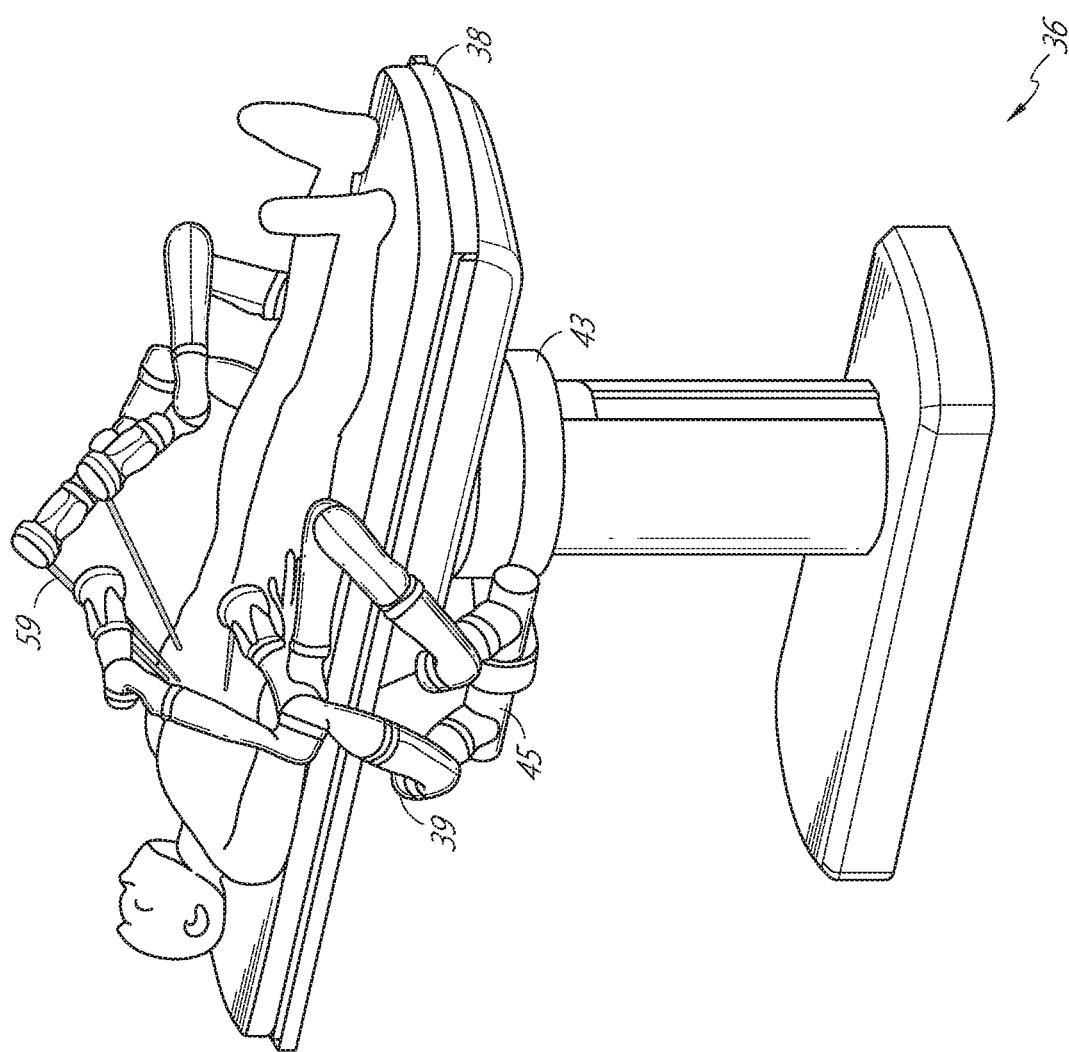
FIG. 9 illustrates an embodiment of a table-based robotic system configured for a laparoscopic procedure.

The robotic arms 39 may be mounted on the carriages 43 through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of the table 38 (as shown in FIG. 6), on opposite sides of the table 38 (as shown in FIG. 9), or on adjacent sides of the table 38 (not shown).

The column 37 structurally provides support for the table 38, and a path for vertical translation of the carriages 43. Internally, the column 37 may be equipped with lead screws for guiding vertical translation of the carriages, and motors to mechanize the translation of the carriages 43 based the lead screws. The column 37 may also convey power and control signals to the carriages 43 and the robotic arms 39 mounted thereon.

The table base 46 serves a similar function as the cart base 15 in the cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

With continued reference to FIG. 6, the system 36 may also include a tower (not shown) that divides the functionality of the system 36 between the table and the tower to reduce the form factor and bulk of the table. As in earlier disclosed embodiments, the tower may provide a variety of support functionalities to the table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 46 for potential stowage of the robotic arms 39. The tower may also include a master controller or console that provides both a user interface for user input, such as keyboard and/or pendant, as well as a display screen (or touchscreen) for preoperative and intraoperative information, such as real-time imaging, navigation, and tracking information. In some embodiments, the tower may also contain holders for gas tanks to be used for insufflation.

Figure 7:
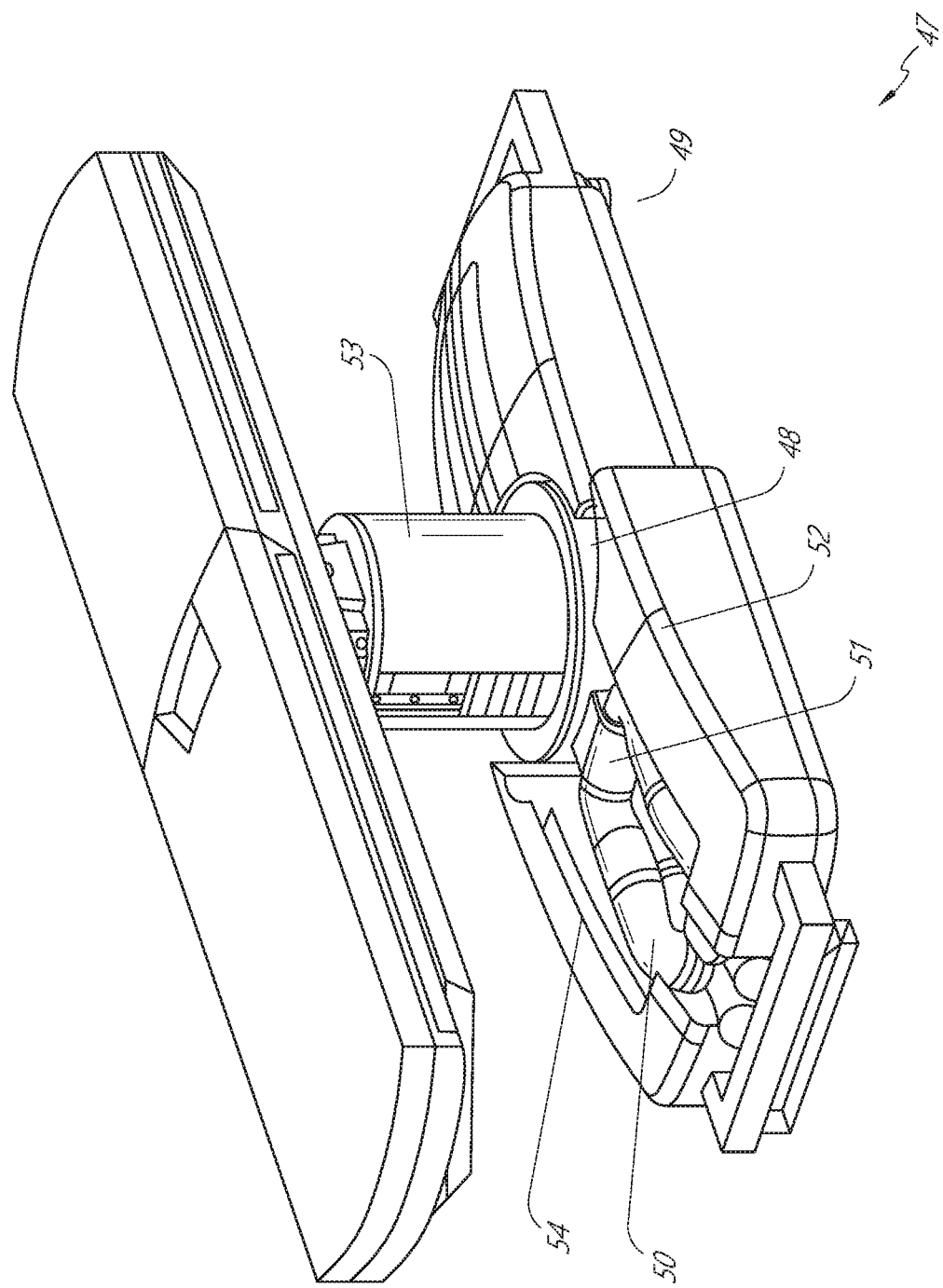
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In the system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and robotic arms 50 around column 53, and closed to stow to protect them when not in use. The base covers 52 may be sealed with a membrane 54 along the edges of its opening to prevent dirt and fluid ingress when closed.

Figure 8:
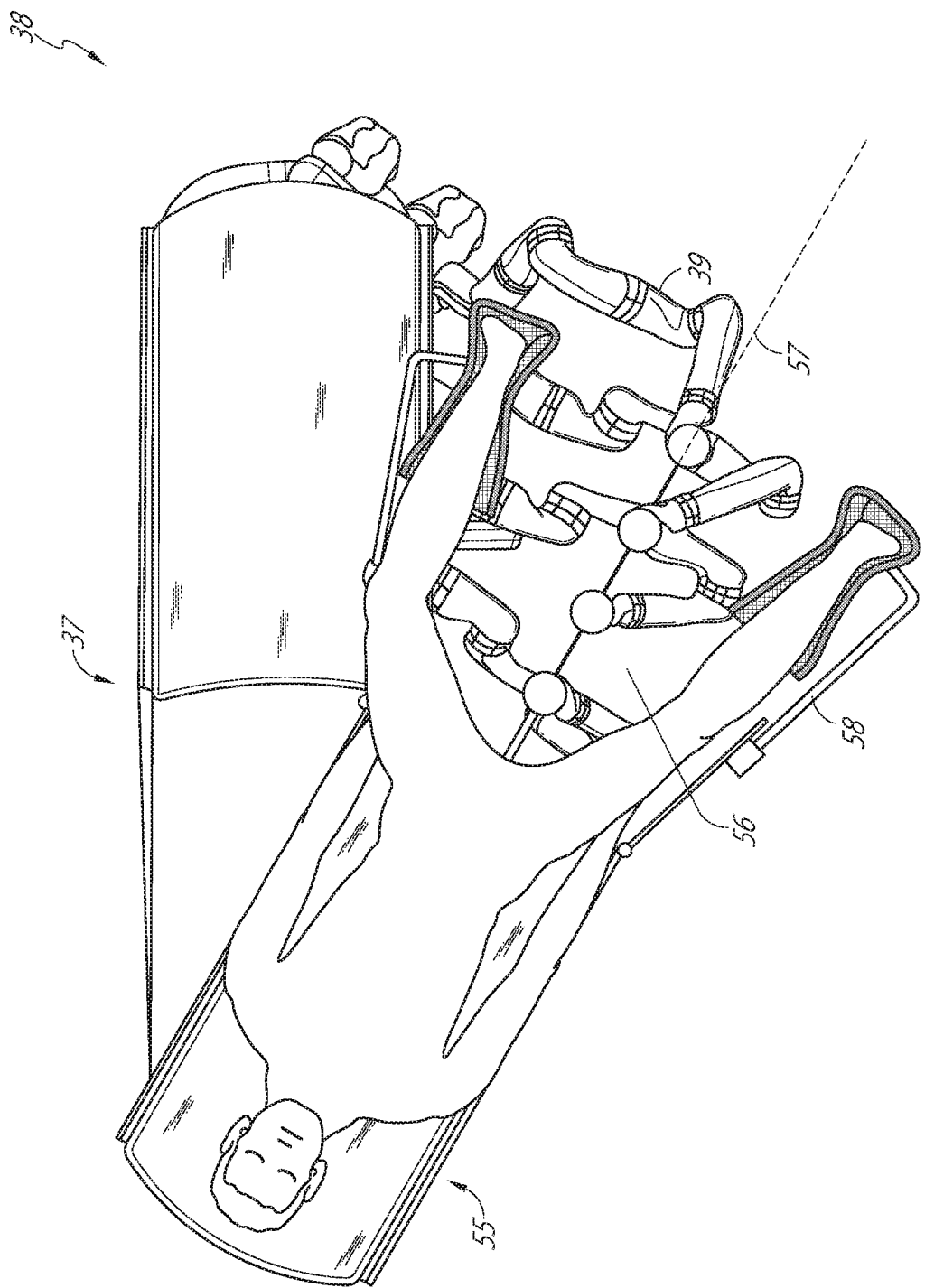
FIG. 8 illustrates an embodiment of a table-based robotic system configured for a ureteroscopic procedure.

FIG. 8 illustrates an embodiment of a robotically-enabled table-based system configured for a ureteroscopic procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
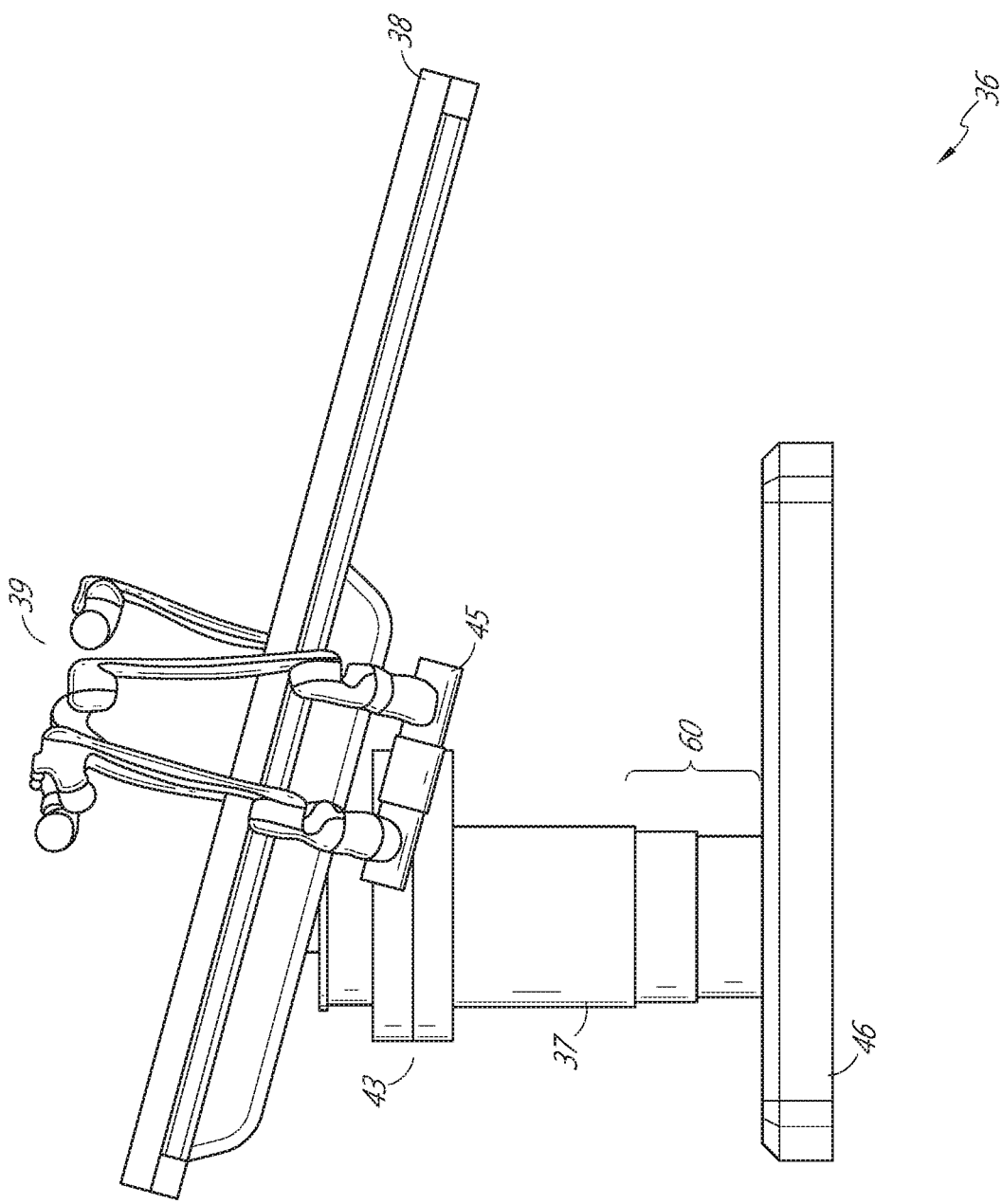
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the robotic arms 39 maintain the same planar relationship with the table 38. To accommodate steeper angles, the column 37 may also include telescoping portions 60 that allow vertical extension of the column 37 to keep the table 38 from touching the floor or colliding with the table base 46.

Figure 11:
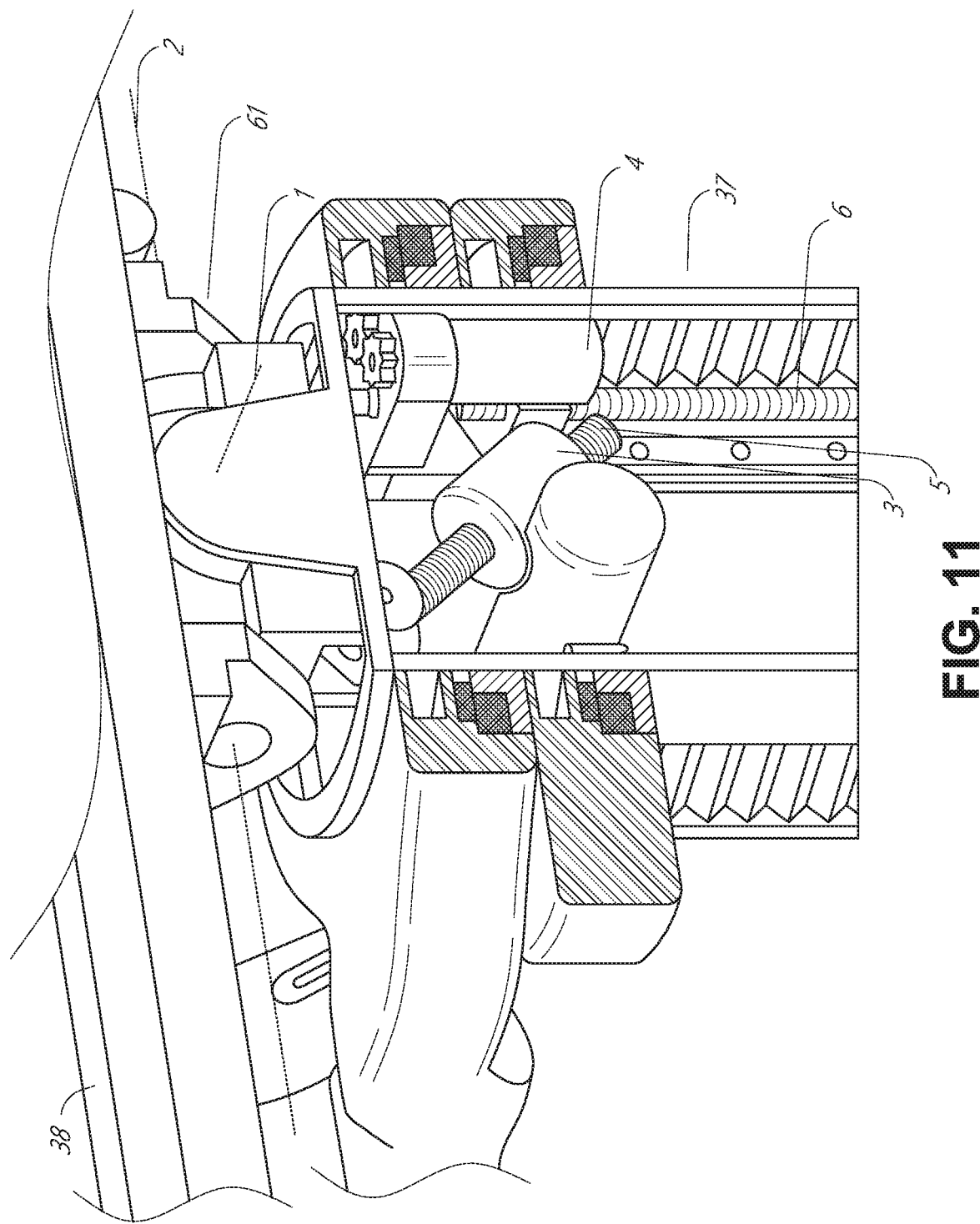
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's upper abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
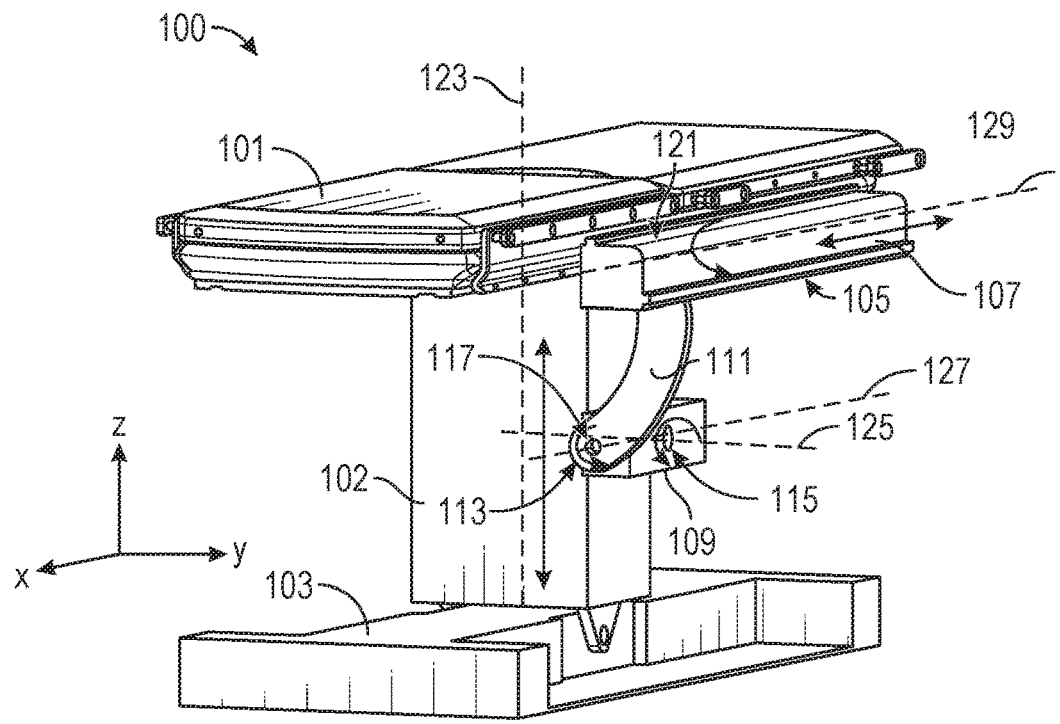
FIG. 12 illustrates an alternative embodiment of a table-based robotic system.
Figure 13:
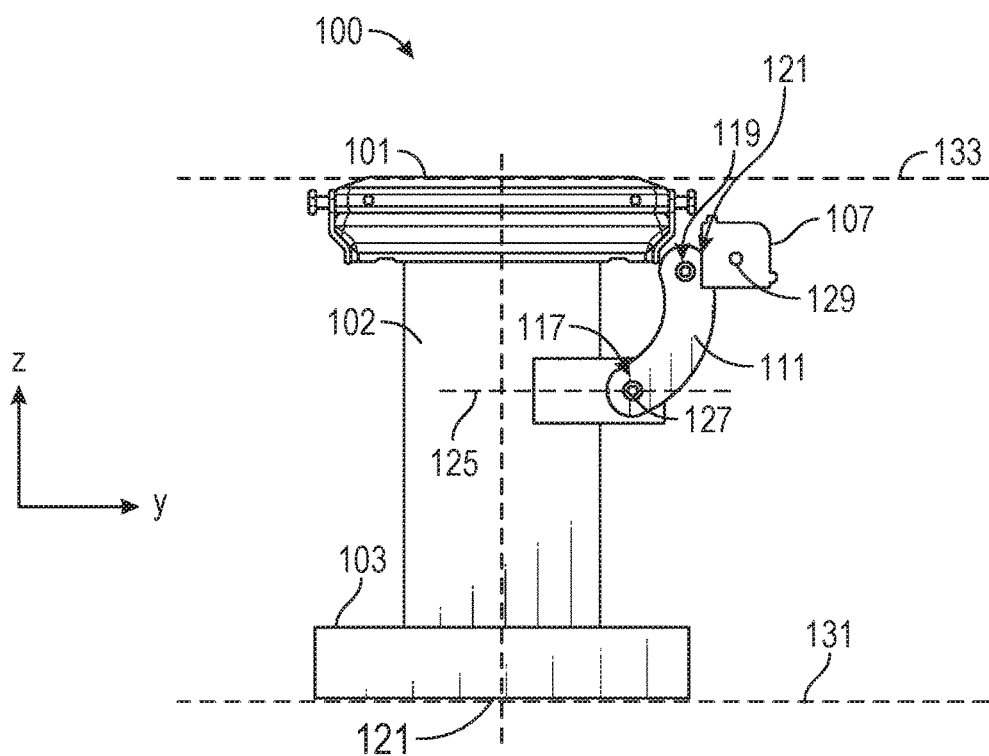
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support 105 can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom (Z-lift) to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
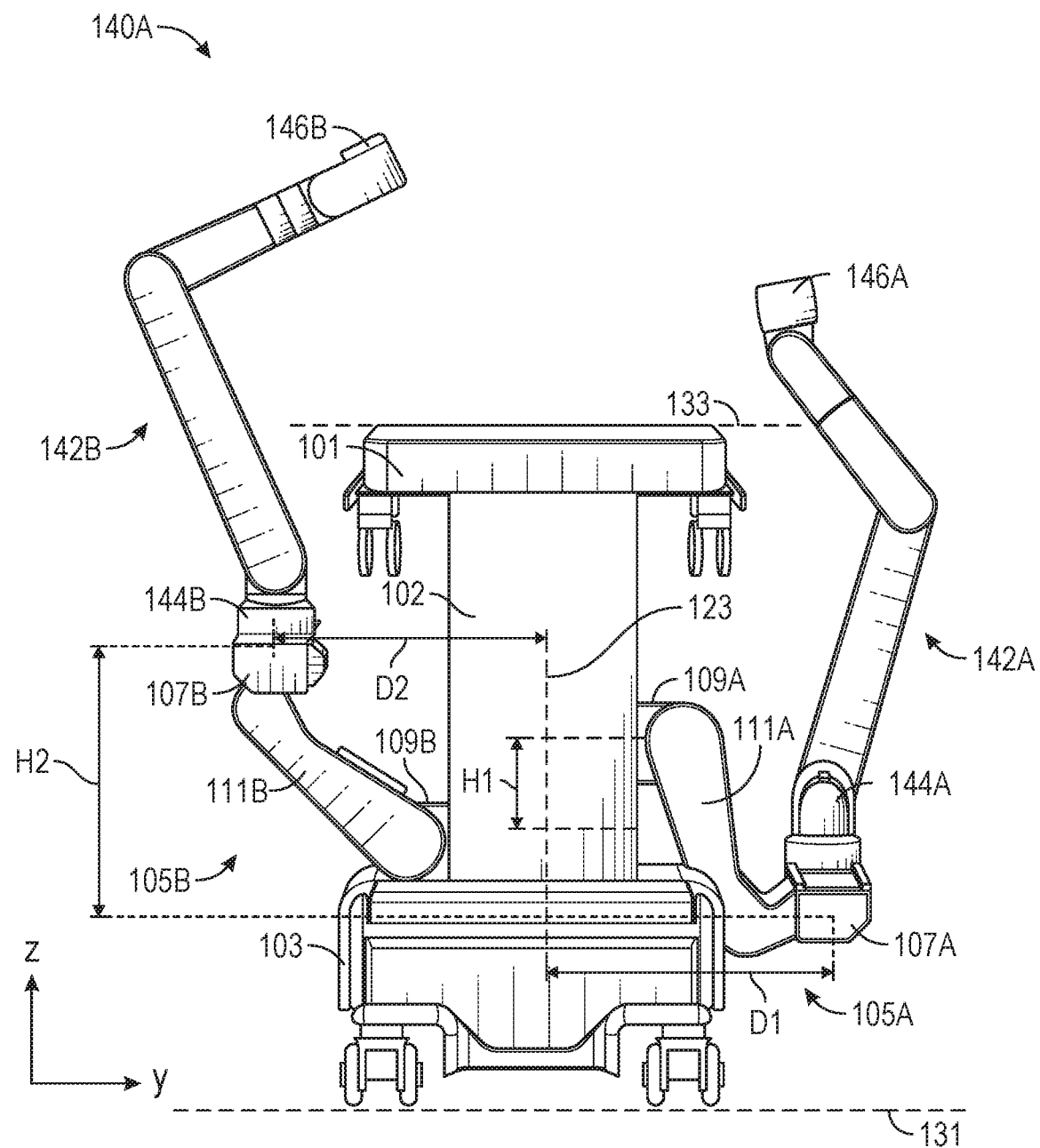
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface.

The end effectors of the system's robotic arms may comprise (i) an instrument driver (alternatively referred to as "instrument drive mechanism" or "instrument device manipulator") that incorporates electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
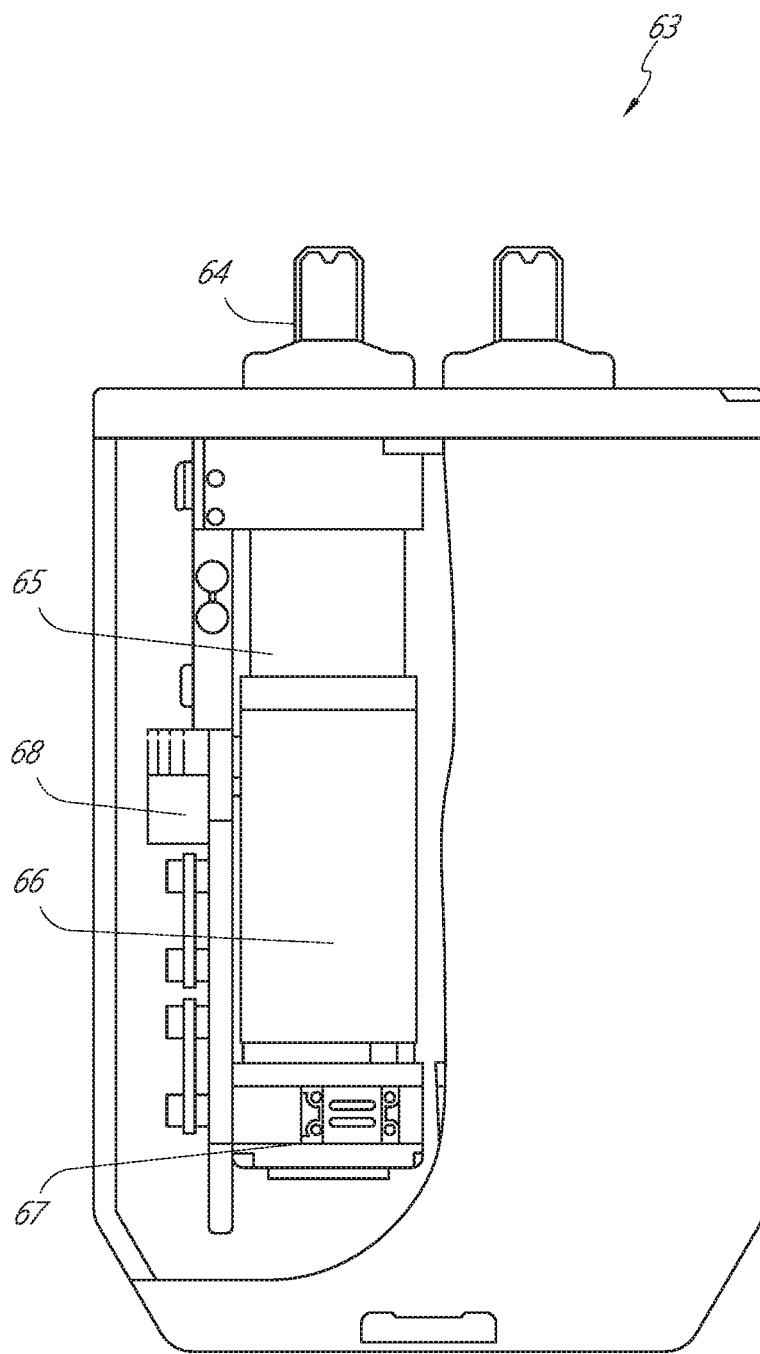
FIG. 15 illustrates an exemplary instrument driver.

FIG. 15 illustrates an example instrument driver. Positioned at the distal end of a robotic arm, instrument driver 62 comprises one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to control circuitry, and control circuitry 68 for receiving control signals and actuating the drive unit. Each drive unit 63 being independently controlled and motorized, the instrument driver 62 may provide multiple (e.g., four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 16:
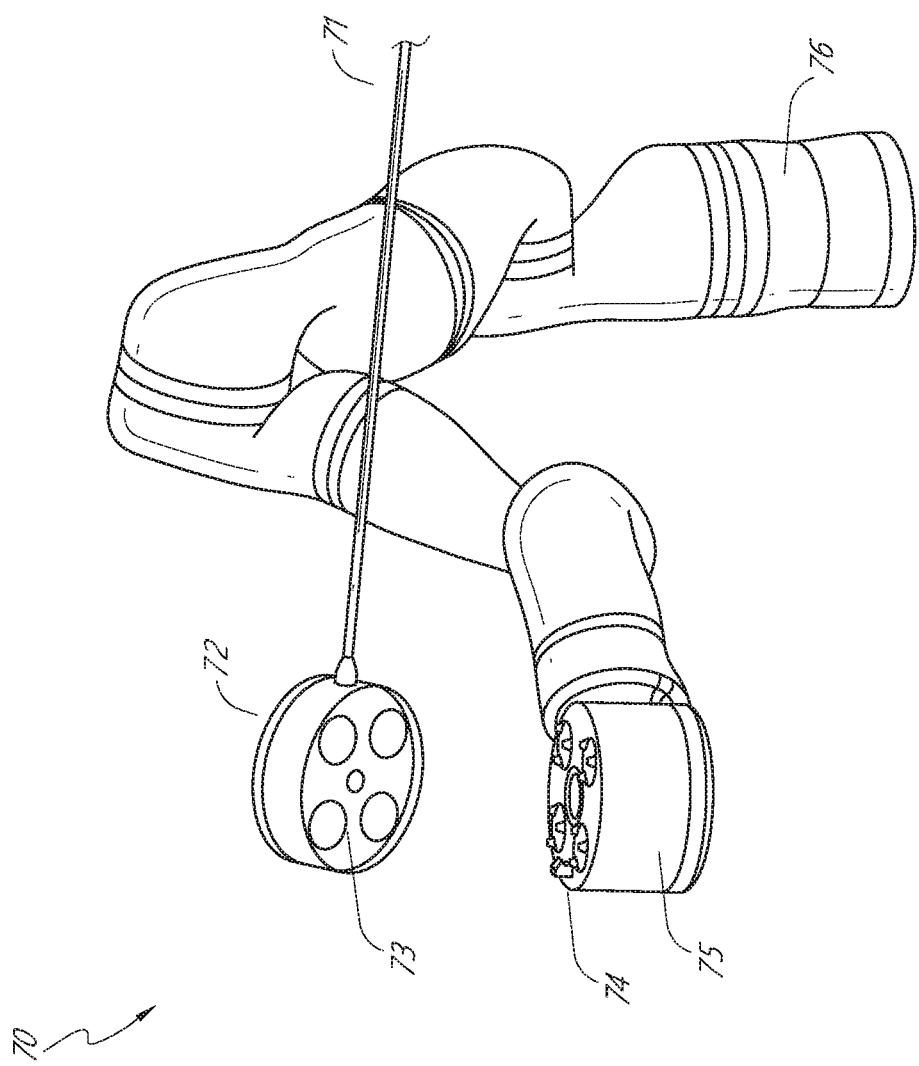
FIG. 16 illustrates an exemplary medical instrument with a paired instrument driver.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of the instrument base 72 may share axes of rotation with the drive outputs 74 in the instrument driver 75 to allow the transfer of torque from the drive outputs 74 to the drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the elongated shaft 71. These individual tendons, such as pull wires, may be individually anchored to individual drive inputs 73 within the instrument handle 72. From the instrument handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at the distal end of the elongated shaft 71, where tension from the tendon causes the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on the drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing therebetween may be altered or engineered for specific purposes, wherein tighter spiraling exhibits lesser shaft compression under load forces, while lower amounts of spiraling results in greater shaft compression under load forces, but limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft 71 may comprise a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include an optical camera. The shaft 71 may also accommodate optical fibers to carry light from proximally-located light sources, such as light emitting diodes, to the distal end of the shaft 71.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft 71. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft 71 during an endoscopic procedure.

Figure 17:
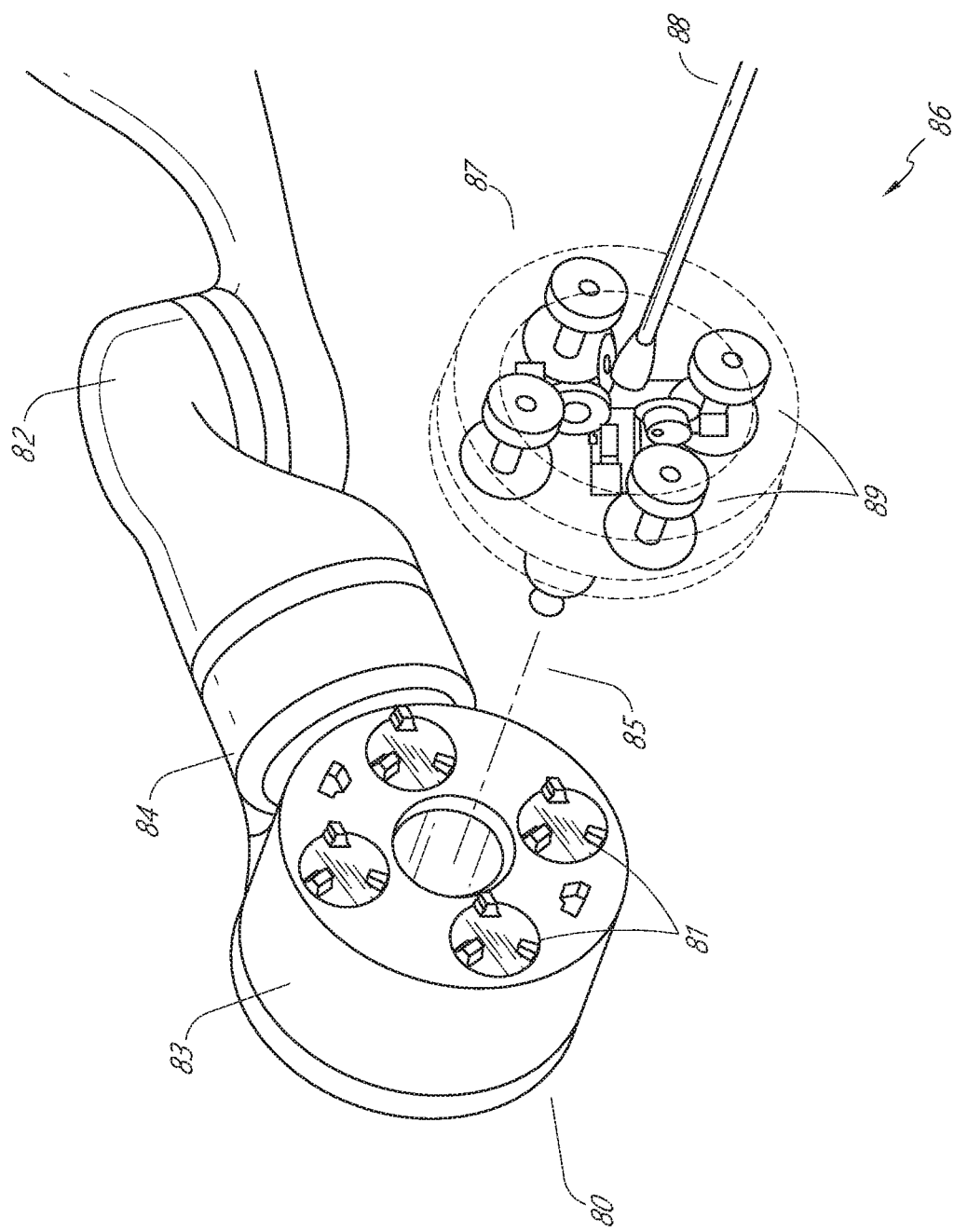
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver 80. Power and controls signals may be communicated from the non-rotational portion 84 of the instrument driver 80 to the rotational assembly 83 through electrical contacts that may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, the instrument shaft 88 extends from the center of the instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
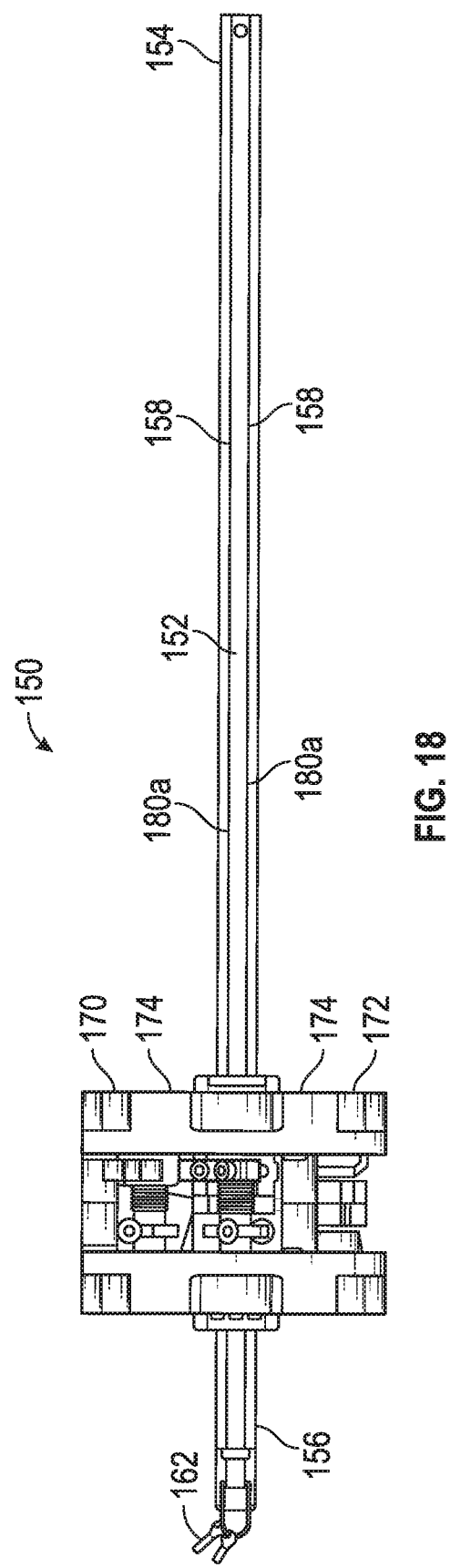
FIG. 18 illustrates an instrument having an instrument-based insertion architecture.

FIG. 18 illustrates an instrument having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver.

In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
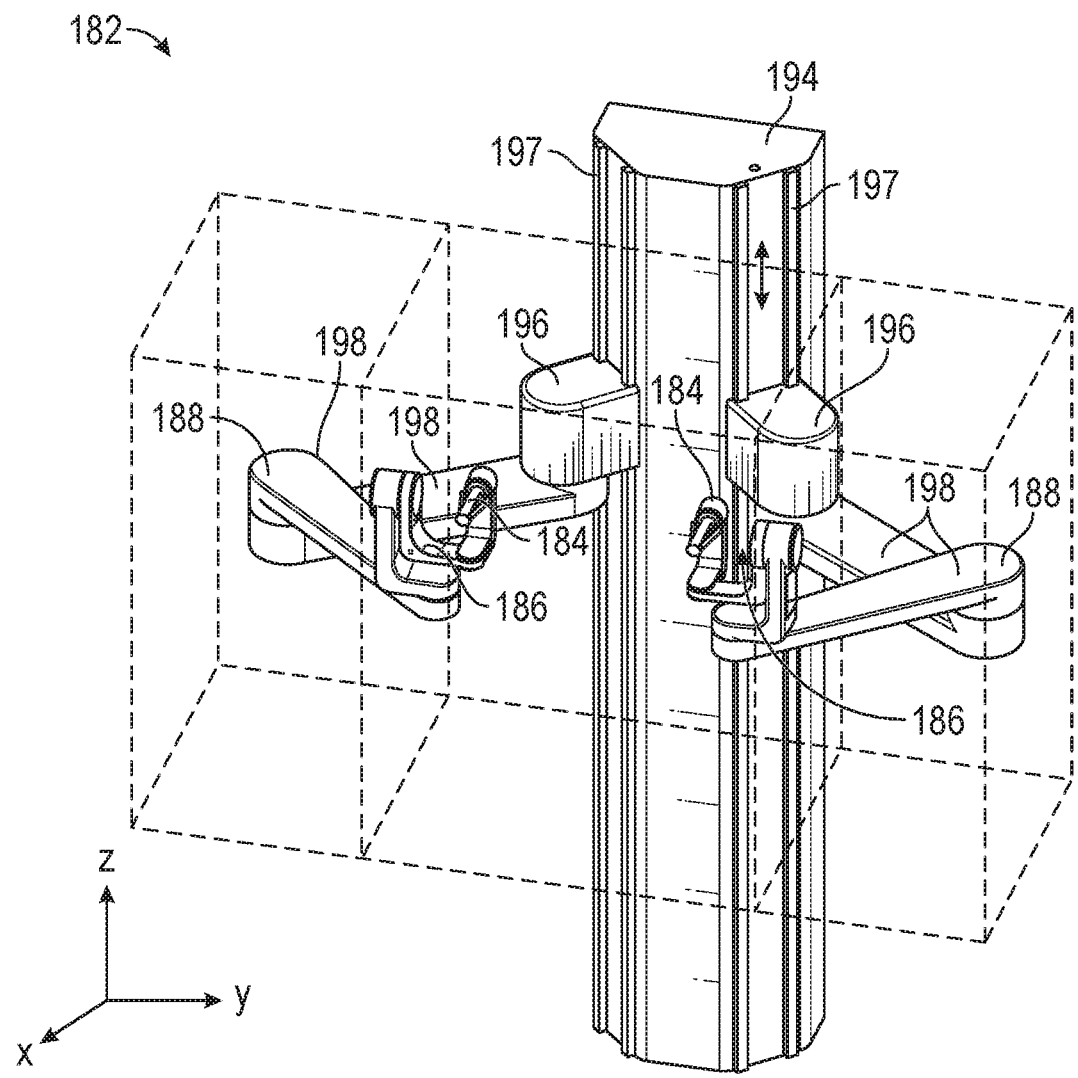
FIG. 19 illustrates an exemplary controller, according to some embodiments.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a selective compliance assembly robot arm (SCARA) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as preoperative mapping, computer vision, real-time EM tracking, and robot command data may be used individually or in combination to achieve a radiation-free operating environment. In other cases, where radiation-based imaging modalities are still used, the preoperative mapping, computer vision, real-time EM tracking, and robot command data may be used individually or in combination to improve upon the information obtained solely through radiation-based imaging modalities.

Figure 20:
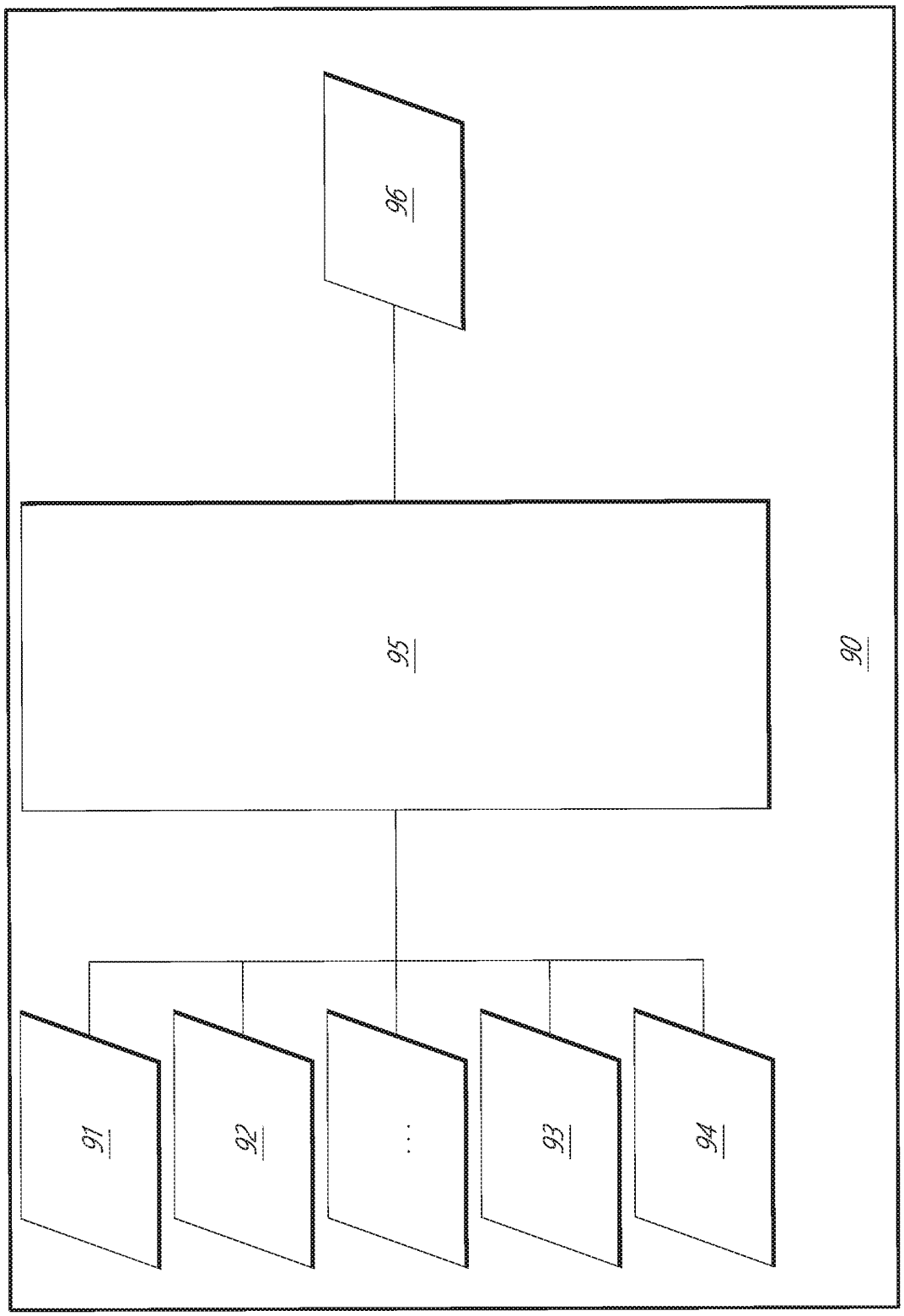
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart 11 shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Preoperative mapping may be used by the localization module 95 to generate model data 91. Preoperative mapping may be accomplished through the use of the collection of low dose CT scans. Preoperative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data (or image data) 92 to the localization module 95. The localization module 95 may process the vision data 92 to enable one or more vision-based (or image-based) location tracking modules or features. For example, the preoperative model data 91 may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intraoperatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking and EM data 93 to generate a real-time location of the endoscope in a global coordinate system that may be registered to the patient's anatomy, represented by the preoperative model. In EM tracking, an EM sensor (or tracker) comprising one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intraoperatively "registered" to the patient anatomy (e.g., the preoperative model) in order to determine the geometric transformation that aligns a single location in the coordinate system with a position in the preoperative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide location data 96 for the robotic system. Device pitch and yaw resulting from articulation commands may be determined during preoperative calibration. Intraoperatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Introduction to Detection of Contact Between a Link and an External Object.

Embodiments of the disclosure relate to systems and techniques for detecting contact between a robotic arm/manipulator and an external object. As described herein, robotic medical systems may include a plurality of robotic arms configured to control the movement of medical tool(s) during a given medical procedure. In order to achieve a desired pose of a medical tool, a robotic arm may be placed into a pose, which may cause the robotic arm to come into contact with an external object, such as, for example, a patient, bedside staff, or inanimate object(s) (e.g., accessories on the bed). If undetected, such contact (also referred to as a "collision") can result in injury to the patient or beside staff and/or damage to the robotic arm or external object(s). By detecting contact between the robotic arm and the external object early enough (e.g., before the contact results in a force greater than a threshold value), injury and/or damage can be reduced or prevented.

One safety consideration relates to when a robotic link (e.g., a portion of robotic arm) comes into contact with an external object. For example, when the robotic arm comes into contact with a patient in an unplanned or accidental manner, harmful forces may be created and/or transferred to the patient. Thus, one challenge with robotic medical systems is detecting contact with surrounding objects and people (including the patient) to ensure that the robotic system can safely operate around people.

Aspects of this disclosure provide systems and techniques for detecting contact between or with links (e.g., of the robotic arms), which can involve the use of one or more sensors. Once contact is detected, the robotic system can take action to reduce further contact. For example, in some implementations the robotic arm can stop further movement upon detection of contact with an external object.

Contact Detection Using a Force Sensing Floating Shell

Figure 21A:
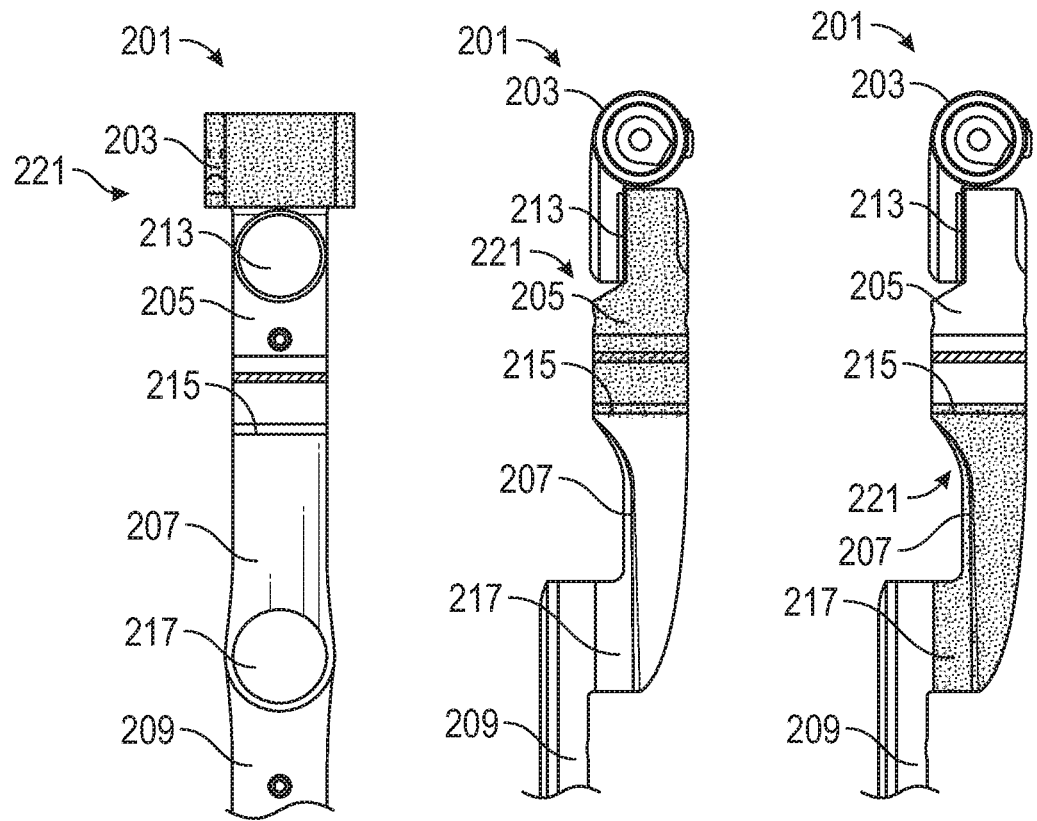
FIGS. 21A and 21B illustrate example robotic links that can form a portion of a robotic arm, in accordance with aspects of this disclosure.
Figure 21B:
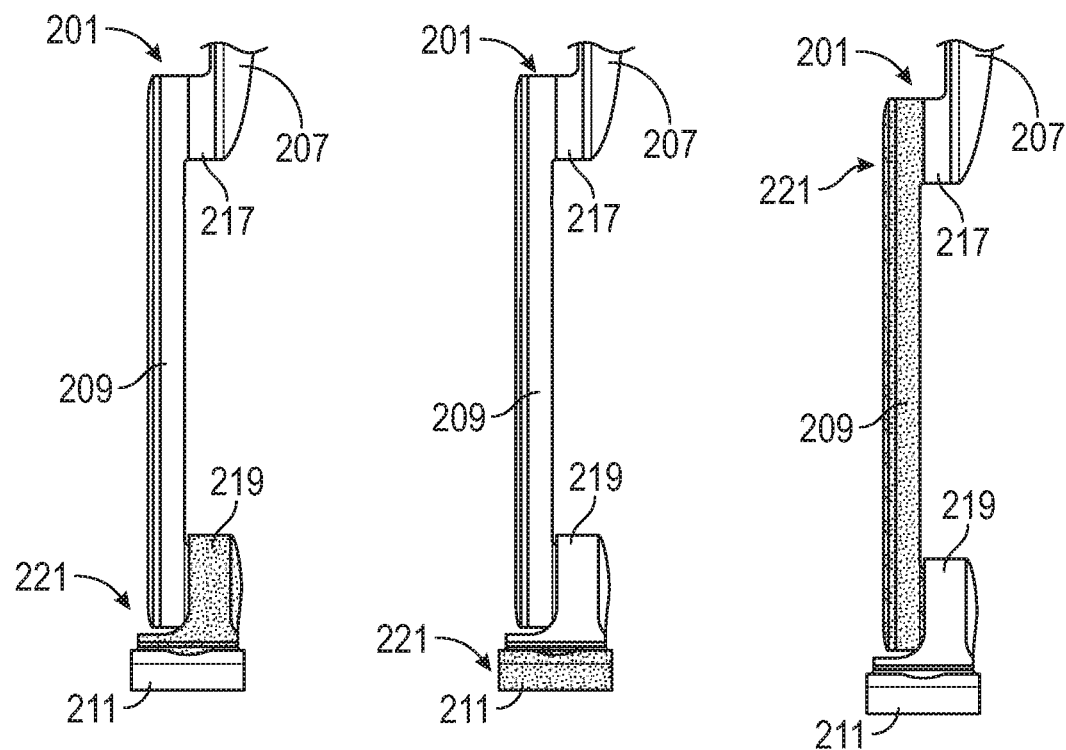

According to aspects of this disclosure, a robotic arm can comprise a plurality of robotic links connected via a series of joints providing a plurality of degrees-of-freedom of movement that enable the robotic arm to be positioned in a variety of different poses or states. FIGS. 21A and 21B illustrate example robotic links that can form a portion of a robotic arm in accordance with aspects of this disclosure. Although examples of robotic links used as a part of a robotic arm are provided herein, aspects of this disclosure also include other types of links (e.g., robotic and non-robotic, medical and non-medical) for which detection of contact with external objects may be desirable.

FIG. 21A illustrates three views of a distal portion of a robotic arm 201, whereas FIG. 21B illustrates three views of a portion of the robotic arm 201 that is proximal to the distal portion of FIG. 21A. With reference to FIGS. 21A and 21B, the robotic arm 201 may include a device manipulator 203, a plurality of links 205, 207, 209, and 211, and a plurality of joints 213, 215, 217, and 219 connecting the device manipulator 203 and the links 205-211. In each of the views illustrated in FIG. 21A, regions 221 of the robotic arm 201 which have a relatively higher likelihood of colliding with a patient are highlighted.

Aspects of this disclosure are directed to an arm component (e.g., one of the robotic links 205-211 or joints 213-219 of FIGS. 21A-21B) that is capable of sensing contact with external objects such as a patient, bedside staff, or other object.

Figure 22:
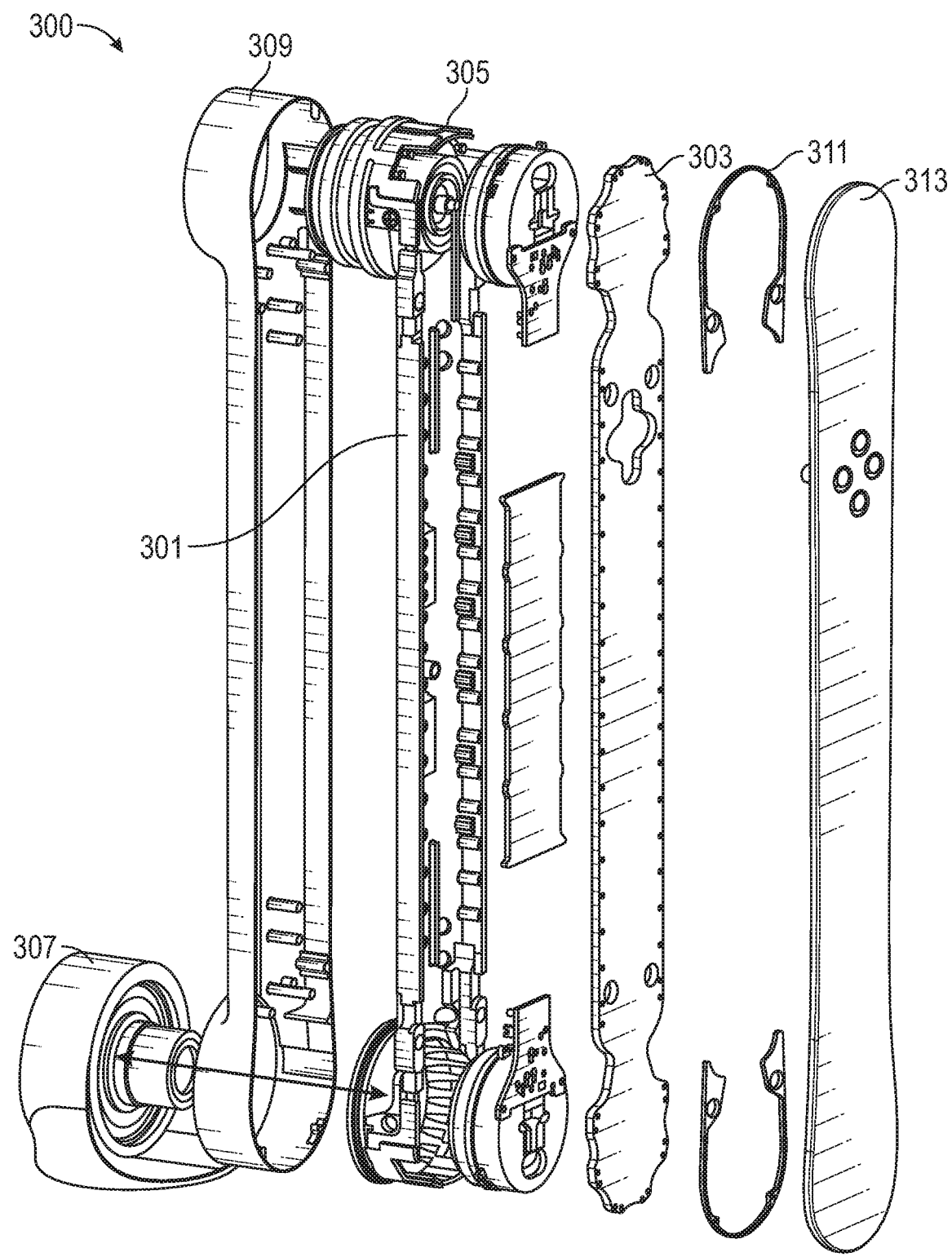
FIG. 22 illustrates an example link including a rigid shell and configured to detect contact with external objects, in accordance with aspects of this disclosure.

In certain implementations, a shell can be suspended around a given link and the relative motion between the shell and inner components/members of the link can be detected using one or more sensors in order to detect contact with an external object. FIG. 22 illustrates an example link 300 including a rigid shell 309 and configured to detect contact with external objects in accordance with aspects of this disclosure. In particular, the link 300 includes a structural link 301, a structural cover 303, a first joint 305, a second joint 307, a shell 309, a pair of reaction paddles 311, and a shell cover 313. For example, the inner components of the link 300 may comprise the structural link 301 and the structural cover 303.

The structural cover 303 can be attached to the structural link 301 to house components of the structural link 301 and form the internal structural connection between the first joint 305 and the second link 305. The shell 309 together with the shell cover 313 are suspended from and surround the structural link 301. As used herein, the shell 309 and shell cover 313 may collectively be referred to simply as the "shell" 309, while the structural link 301 and structural cover 303 may collectively be referred to simply as the structural link 301 or a manipulatable link, unless the context clearly indicates otherwise.

The shell 309 may be connected to the structural link 301 via a force-sensing connection. Because the shell 309 surrounds the structural link 301, when the link 300 contacts an external object, the object will come into contact with the shell 309. Thus, the force-sensing connection can detect contact between the shell 309 and the external object by measuring changes in the force between the shell 309 and the structural link 301 caused by the link 300 coming into contact with the external object. The shell 309 may also be sufficiently rigid such that, upon contact with an external object, the shell 309 engages the force-sensing connection. Advantageously, by using a rigid shell 309 the force and relative movement between the shell 309 and the structural link 301 can be sensed in all three directions.

The force-sensing connection may be implemented in a variety of different manners in accordance with aspects of this disclosure. For example, the force-sensing connection can include one or more of the following: traditional load cells, force sensing resistors, and/or any component capable of sensing force (or displacement, when combined with a spring).

Figure 23:
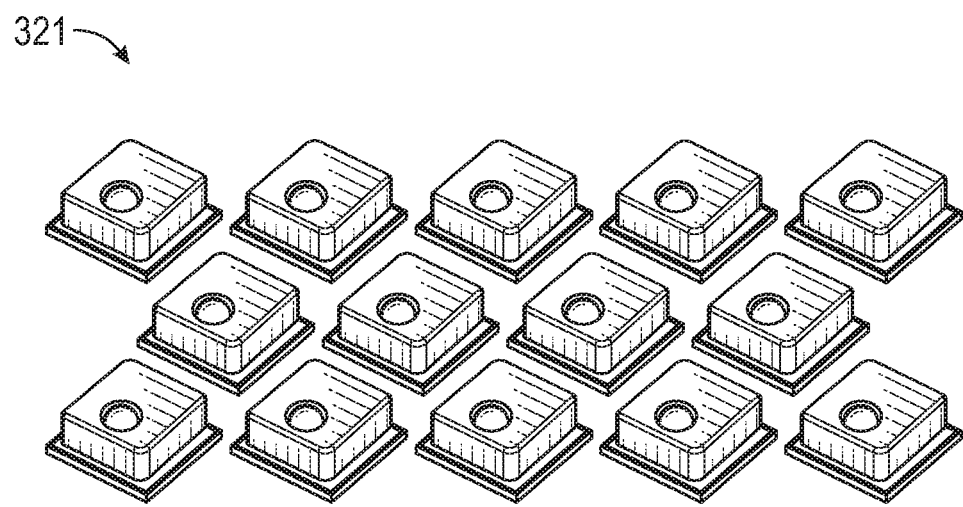
FIG. 23 illustrates one example of a force-sensing connection that can be used in the link of FIG. 22, in accordance with aspects of this disclosure.

FIG. 23 illustrates one example of a force-sensing connection that can be used in the link 300 of FIG. 22 in accordance with aspects of this disclosure. In particular, the force-sensing connection can include a plurality of shell sensors 321 (e.g., fourteen shell sensors in the illustrated embodiment), which can be disposed between the structural link 301 and the shell 309.

Figure 24A:
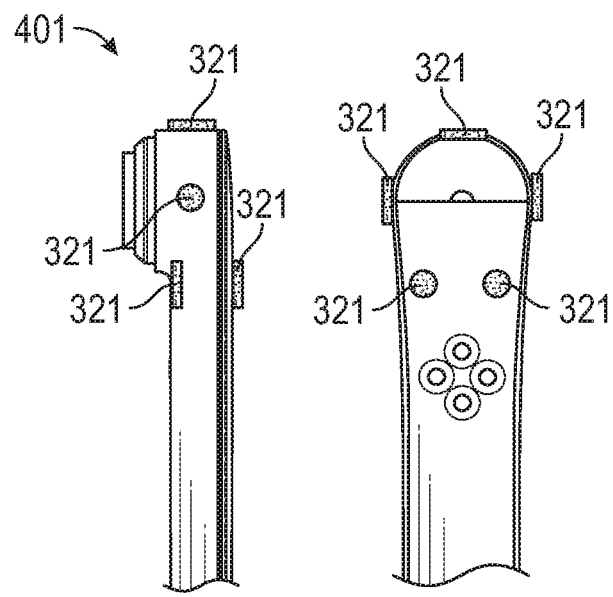
FIG. 24A illustrates two views of an embodiment in which fourteen sensors are included in a link, in accordance with aspects of this disclosure.

In some embodiments, the sensors 321 are distributed throughout the link 300 in between the shell 309 and the structural link 301. For example, the shell 309 can be suspended over the structural link 301 via the sensors 321. Depending on the implementation, the link 300 can include one, two, three, four or more sensors 321 distributed along a robotic arm link. FIG. 24A illustrates two views of an embodiment in which fourteen sensors 321 are included in a link 401 in accordance with aspects of this disclosure. In particular, FIG. 24A illustrates a side and front view of one end of the link 401 which includes seven sensors 321. The link 401 may be substantially symmetric at both ends of the link 401, thereby including a total of fourteen sensors 321 in the link 401.

Figure 24B:
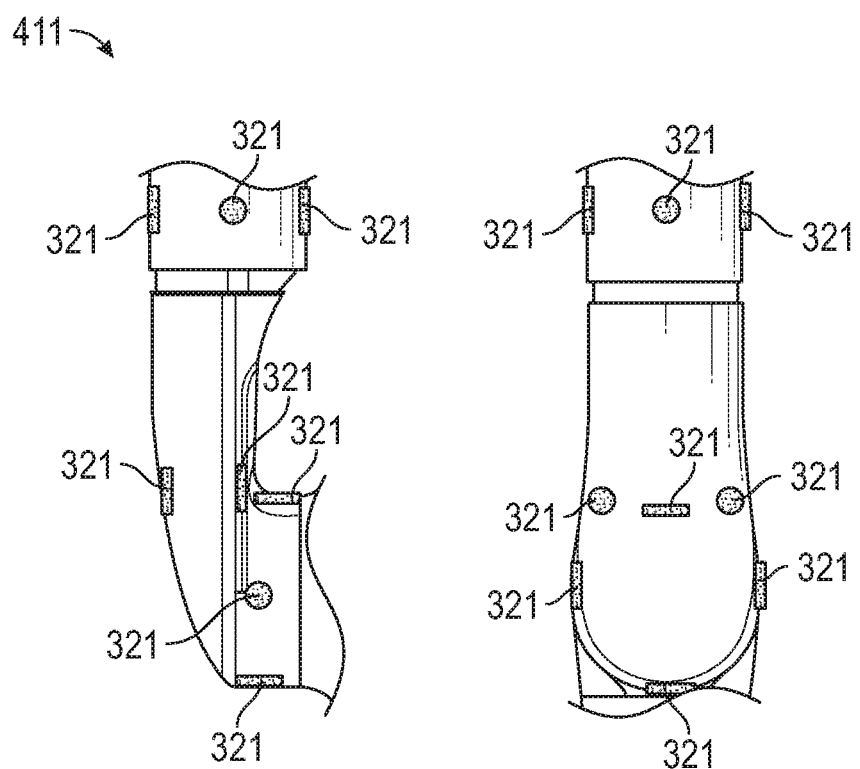
FIG. 24B illustrates two views of an embodiment in which twelve sensors are included in a link, in accordance with aspects of this disclosure.

FIG. 24B illustrates two view of an embodiment in which twelve sensors 321 are included in a link 411 in accordance with aspects of this disclosure. In some implementations, a robotic arm may include the link 401 and the link 411, with the link 401 positioned proximal to the link 411. In particular, FIG. 24B illustrates a side and front view of the link 411 which includes twelve sensors 321. The link 401 may be substantially symmetric at both ends of the link 401, thereby including a total of fourteen sensors 321 in the link 401. In a number of implementations, the plurality of sensors 321 can be configured to support the rigid shell without being fixed to the rigid shell. In some implementations, the link 401, 411 may further include one or more supports configured to support the rigid shell relative to the structural link. For example, the one or more supports can include spring(s), flexure(s), and/or suspension(s).

Although FIGS. 24A and 24B illustrate embodiments of links 401, 411 including a plurality of sensors 321, in other implementations the link can include a single sensor configured to sense force and/or displacement between the structural link 301 and the shell 309 in multiple directions. Using signals received from the sensor(s) 321, the robotic system can be configured to detect a direction of the contact between the shell 309 and the external object. The robotic system can also measure a magnitude of a force resulting from the contact between the shell 309 and the external object based on the signal from the sensor(s) 321. Based on the placement of the plurality of sensors 321 within the links 401 and 411, the robotic system can also be configured to detect a torque applied to the link. For example, if a torque is applied to the shell 309, certain sensors 321 on one side of the link 401, 411 may be compressed. Based on the positions of and forces sensed by the sensors 321 being compressed, the robotic system can determine a torque applied to the link 401, 411.

Figure 25:
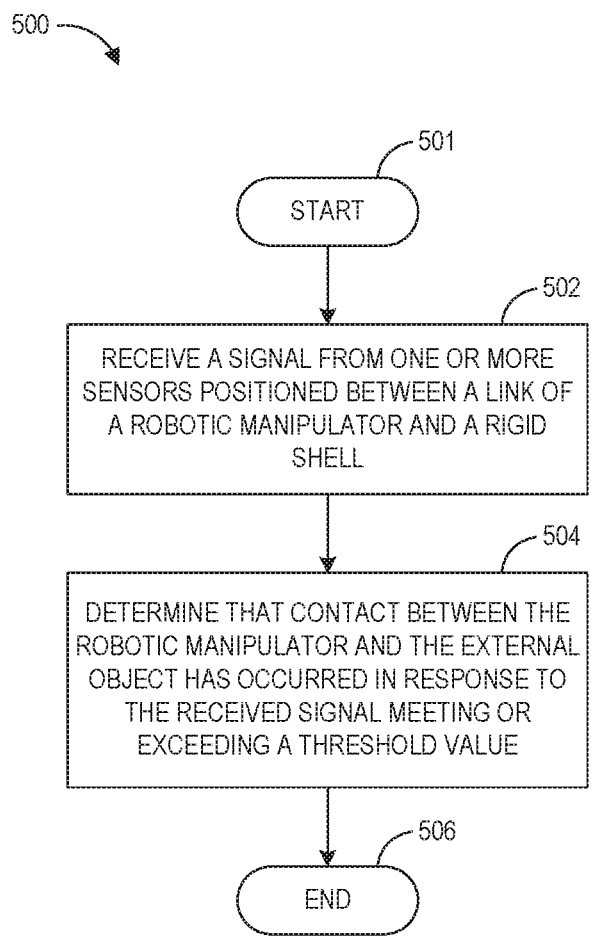
FIG. 25 is a flowchart illustrating an example method operable by a surgical robotic system, or component(s) thereof, for detecting contact between a robotic manipulator and an external object, in accordance with aspects of this disclosure.

FIG. 25 is a flowchart illustrating an example method 500 operable by a surgical robotic system, or component(s) thereof, for detecting contact between a robotic arm/manipulator and an external object in accordance with one or more aspects of this disclosure. It is to be appreciated that the steps of method 500 illustrated in FIG. 25 may be performed by one or more processors of a surgical robotic system. For convenience, the method 500 is described as performed by a processor of the system.

The processor may be included as a part of a system, including a robotic manipulator including a link, a rigid shell configured to overlay the link, and one or more sensors positioned between the rigid shell and the link. The one or more sensors are configured to detect contact between one or more external objects and the rigid shell in at least two or more directions. The system may further include at least one computer-readable memory in communication with the processor and having stored thereon computer-executable instructions to cause the set of processors to perform the method 500.

The method 500 may begin at block 501. At block 502, the processor may receive a signal from the one or more sensors positioned between the manipulatable link of the robotic manipulator and the rigid shell configured to overlay the link. The received signal is indicative of the degree of contact between the rigid shell and the one or more sensors.

At block 504, the processor may determine that contact between the robotic manipulator and the external object has occurred in response to the received signal meeting or exceeding a threshold value. In some implementations, the processor can also detect a direction of the contact between the rigid shell and the external object based on the received signal. The processor can also measure a magnitude of a force and/or torque resulting from the contact between the rigid shell and the external object based on information in the signal (e.g., data in the time or frequency domain) received from the one or more sensors. The processor may also be configured to measure a direction of relative motion between the rigid shell and the link based on the received signal.

In certain embodiments, the processor may also be configured to determine the location in space of the external object based on signal(s) from sensor(s) indicative of the detected contact and prevent movement of the robotic arm (or other robotic arms) to the location of the contact by updating a collision model to avoid future contact in the same area. Such information may include which sensors are activated by the contact and/or directional information detected by a given sensor. As used herein, a collision model may be a model of object(s) within the environment which may be at risk of a collision with the robotic arms. The robotic system can prevent movement of the robotic arms which would result in collisions with object(s) modeled in the collision model. The method 500 may end at block 506.

Figure 26:
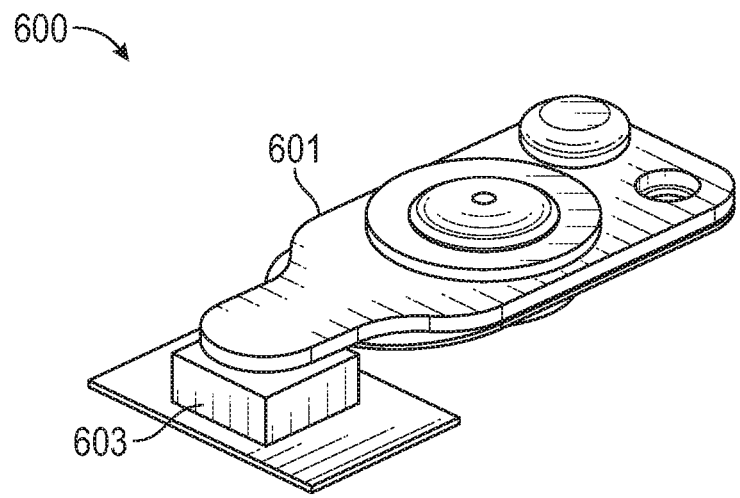
FIG. 26 illustrates an embodiment of a beam flexure sensor, in accordance with aspects of this disclosure.

The one or more sensors 321 that are provided in the link 300, 401, or 411 can include: traditional load cells, force sensing resistors, strain gauges, and/or capacitive sensors, etc. In one implementation, the one or more sensors 321 comprise beam flexure type sensors 600 (also referred to a spring or diving board sensor). FIG. 26 illustrates an embodiment of a beam flexure sensor 600 in accordance with aspects of this disclosure. In this implementation, the sensor 600 comprises a beam flexure 601 configured to contact an underlying force sensor 603. Upon a force being applied to the shell 309, the shell applies a force to the sensor through the beam flexure 601 which then applies a force to the force sensor 603 (which may be scaled from the original force). Such motions (which can include micromotions) will therefore allow the sensor 603 to detect that contact with an external object has occurred. Based on the detection of contact with an external object, the robotic system can take actions (e.g., stop motion of the robotic arm) to reduce the contract or prevent further contact.

Figure 27:
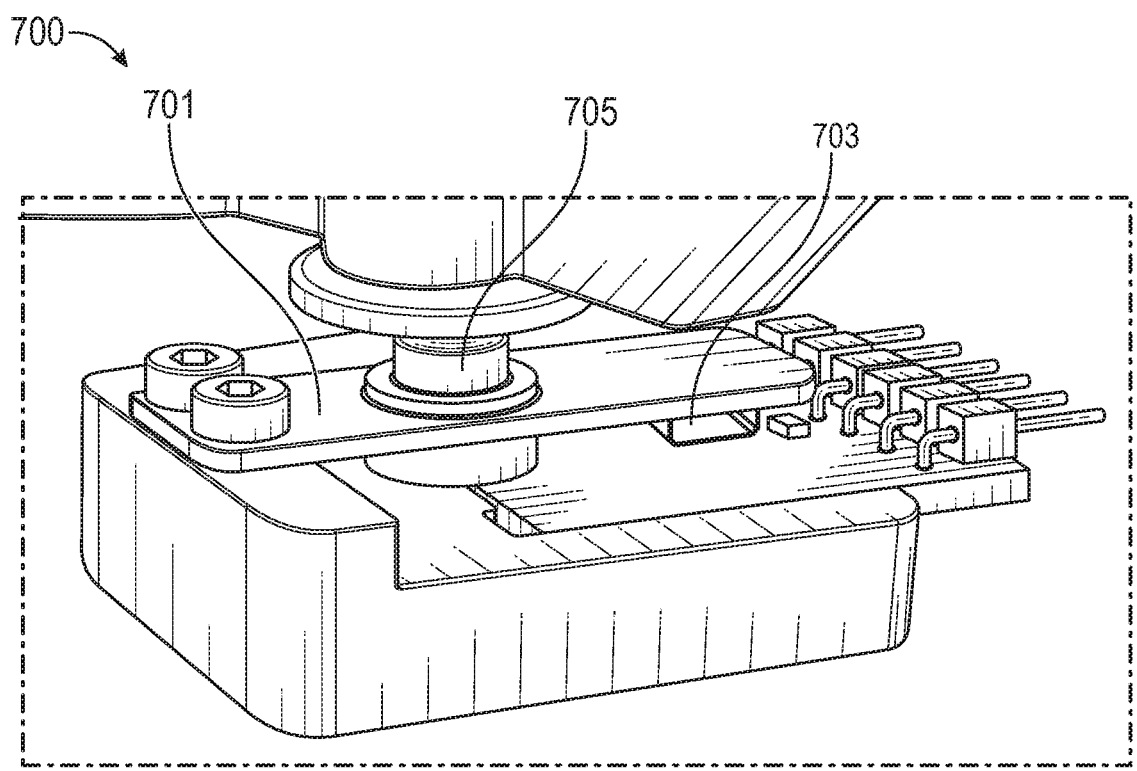
FIG. 27 illustrates another embodiment of a beam flexure sensor, in accordance with aspects of this disclosure.

FIG. 27 illustrates another embodiment of a beam flexure sensor 700 in accordance with aspects of this disclosure. In this implementation, the sensor 700 comprises a beam flexure 701 that is configured to contact an underlying force sensor 703, and a contact point 705 at which the beam flexure 701 is configured to contact the shell 309. Although not illustrated, the sensor 700 can further include a circuit board configured to receive an output signal from the force sensor 703 and output a signal indicative of the force applied to the contact point 705. In some implementations, the force sensor 703 may be mounted on the circuit board. The beam flexure 701 may comprise a first end (e.g., on the left side of FIG. 27) that is fixed and a second end (e.g., on the right side of FIG. 27) coupled to the force sensor 703. The contact point 705 is located between the first and second ends of the beam flexure 701. Accordingly, the force exerted on the force sensor 703 is proportional to or otherwise indicative of the force applied to the contact point 705. In combination with the contact point 705, the beam flexure 701 can be configured to scale a force applied to the sensor 700 and isolate the sensor 703 from shear forces applied to the shell 309. In certain implementations, the contact point 705 may function as a load concentrator configured to control a point at which the shell 309 applies a force to the sensor 700 (e.g., the point at which the force is applied to the beam flexure 701).

The specific location of the contact point 705 between the first and second ends will affect the amount of leverage provided by contact of an external object with the shell 309 onto the force sensor 703. For example, when the contact point 705 is located closer to the second end with the force sensor 703, more of the force applied to the contact point 705 will be transmitted to the force sensor 703 than when the contact point 705 is located closer to the fixed first end. Thus, the location of the contact point 705 can be selected to map the range of forces expected to be received by the shell 309 onto the range of forces detectable by the force sensor 703. By reducing the forces using the beam flexure 701, the force sensor 703 can effectively measure greater forces applied to the shell 309 by reducing the received force onto the range of forces measurable by the force sensor 703.

Aspects of this disclosure provide a number of advantages for the detection of contact between a link and an external object. For example, aspects of this disclosure are advantageous over systems that measure torque (either directly with a torque sensor, or through current or control loop disturbances) as the sensitivity of implementation of this disclosure do not decrease as the applied force vector approaches the torque axis, as is the case in torque sensing systems. Similarly, systems that mount the entire robot on load cells (as is common in some industrial robots) may have similar drawbacks to torque-based measurement systems.

Additionally, by using a shell 309 to detect contact with an external object as described herein, the system can advantageously sense contact on the entire surface of the link. In contrast, implementations which employ a film to sense contact may not be able to sense or detect contact with an external object at locations where the film is not applied to the link(s).

Another advantage of aspects of this disclosure includes allowing for the system to sense the total amount of contact force over the entire surface of a given link, to allow a certain amount of light incidental contact without interrupting a medical procedure. This is advantageous over systems that are not able to distinguish between a small amount of incidental force and larger forces that risk injury and/or damage.

Yet another advantage of aspects of this disclosure is the compact form factor enabled by the shell compared to systems that surround the robot in pressure-sensitive gas-filled bladders.

Contact Detection Using a Film

Figure 28:
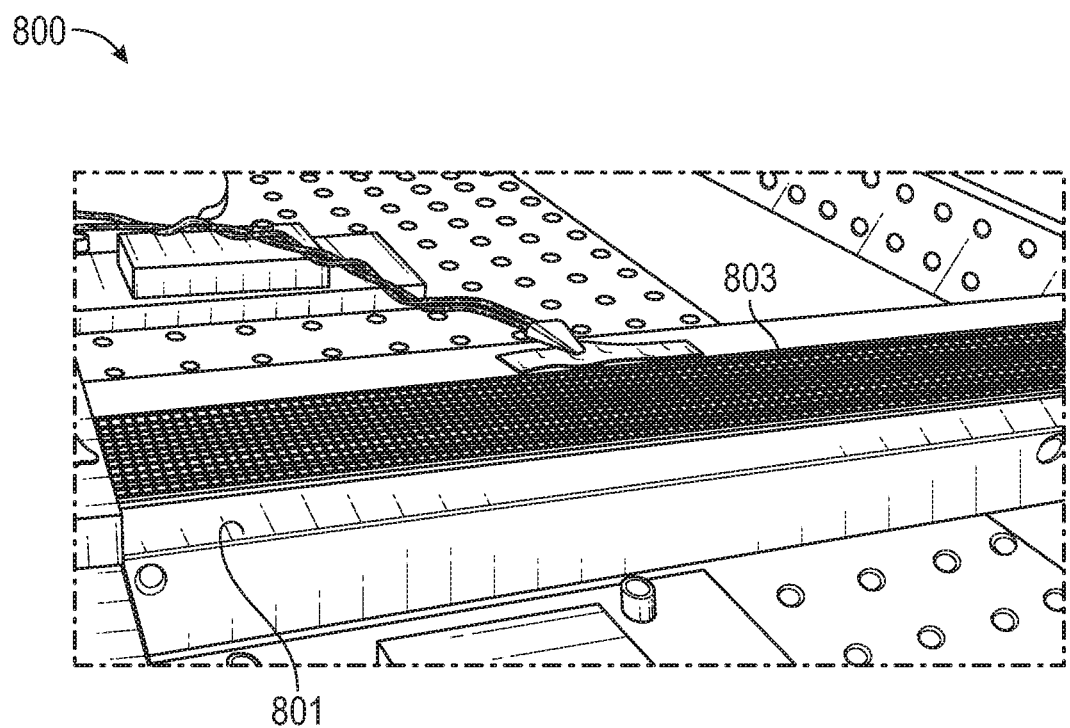
FIG. 28 illustrates an example robotic link that can form a portion of a robotic arm in accordance with aspects of this disclosure.

In certain implementations, a coating or film of sensors can be adhered to a surface of a link (e.g., a robotic arm link). FIG. 28 illustrates an example robotic link 800 that can form a portion of a robotic arm in accordance with aspects of this disclosure. In particular, the link 800 includes a structural link 801 and a film 803 applied to an external surface of the structural link 801. Depending on the implementation, the film 803 can comprise various types of force sensors. For example, technologies which can be used in the film 803 include: force sensing resistors (FSR), capacitive sensors, proximity sensors, and/or others.

In certain implementations, the film 803 may be attached to surfaces of the link 800 that are more likely to contact external objects (e.g., the regions 221 illustrated in FIGS. 21A and 21B). By detecting contact with external objects using the film 803, the robotic system can respond to the detected contact to prevent applying an unacceptably high load onto the external object (e.g., an inanimate object such as medical accessories or a bed, beside staff, or the patient).

By applying such a film 803 to a robotic arm, the robotic system can detect contact between an external object and the robotic arm and prevent further movement in the direction of the contact with the external object. In addition, the robotic system can also determine the location in space of the external object based on the detected contact and prevent movement of the robotic arm (or other robotic arms) to the location of the contact by updating a collision model to avoid future contact in the same area. The robotic system can prevent movement of the robotic arms which would result in collisions with object(s) modeled in the collision model.

The use of a force sensing film 803 in accordance with aspects of this disclosure allows for the maximization of a robot's collision free workspace by allowing the robot (e.g., a robotic arm) to move until it collides with an external object and then stop. This allows for a larger workspace than might otherwise be feasible with force sensing solutions that occupy a larger volume around the structural link (e.g., systems that surround the robot in pressure-sensitive gas-filled bladders).

In contrast to systems that use force or torque sensors positioned in robotic arm joints, aspects of this disclosure which employ force sensing films do not experience a decrease as the applied force vector approaches the torque axis, as is the case in torque sensing systems. Similarly, systems that mount the entire robot on load cells (as is common in some industrial robots) may have similar drawbacks to torque-based measurement systems.

The advantage of an increased collision-free workspace is also apparent compared to systems which artificially limiting a robot's workspace such that it can never contact the patient or accessories. Since such artificial limitations cannot precisely define the locations of external objects, implementations which use such artificial limitations can dramatically limit the workspace and cause user irritation due to unachievable movements and/or poses of the robotic arms. In related aspects, force sensing film 803 may be used in conjunction with one or more sensors 321 that are provided in a manipulatable link, wherein the one or more sensors can include: traditional load cells, force sensing resistors, strain gauges, and/or capacitive sensors, etc.

4. Implementing Systems and Terminology.

Implementations disclosed herein provide systems, methods and apparatus for detecting contact between a link and an external object.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The detection of contact between a link and an external object functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A robotic arm, comprising:
   a link;
   a rigid shell formed over the link; and
   one or more sensors configured to detect contact between an external object and the rigid shell, wherein the one or more sensors are further configured to measure at least one of:
      a magnitude of a force applied to the link,
      a direction of a force applied to the link, or
      a torque applied to the link.

2. The robotic arm of claim 1, wherein the external object comprises one or more of: a patient, a clinician, or an inanimate object.

3. The robotic arm of claim 1, wherein the one or more sensors are positioned in an interstitial space between the link and the rigid shell.

4. The robotic arm of claim 1, wherein the one or more sensors are configured to measure the magnitude.

5. The robotic arm of claim 1, wherein the one or more sensors are configured to measure the direction.

6. The robotic arm of claim 1, wherein the one or more sensors are configured to measure the torque.

7. A robotic arm, comprising:
   a link;
   a rigid shell formed over the link; and
   one or more sensors configured to detect contact between an external object and the rigid shell, wherein the one or more sensors are further configured to measure a relative position of the rigid shell relative to the link.

8. The robotic arm of claim 7, further comprising: a support configured to support the rigid shell relative to the link, wherein the support comprises one or more of: a spring, a flexure, or a suspension.

9. The robotic arm of claim 7, wherein the one or more sensors are further configured to measure a direction of relative motion between the rigid shell and the link.

10. The robotic arm of claim 9, wherein the one or more sensors are further configured to determine a direction of a force applied to the rigid shell.

11. A robotic arm, comprising:
    a link;
    a rigid shell formed over the link; and
    a plurality of sensors configured to detect contact between an external object and the rigid shell, wherein the plurality of sensors comprises at least one of:
       a plurality of circuit board mounted force sensors,
       a plurality of strain gauges,
       a plurality of force sensing resistors, or
       a plurality of capacitive sensors.

12. The robotic arm of claim 11, wherein the plurality of sensors comprises the plurality of circuit board mounted force sensors.

13. The robotic arm of claim 11, wherein the plurality of sensors comprises the plurality of strain gauges.

14. The robotic arm of claim 11, wherein the plurality of sensors comprises the plurality of force sensing resistors.

15. The robotic arm of claim 11, wherein the plurality of sensors comprises a plurality of capacitive sensors.

16. A robotic arm, comprising:
a link;
a rigid shell formed over the link; and
a plurality of sensors configured to detect contact between an external object and the rigid shell, the plurality of sensors being positioned at different locations of the link.

17. The robotic arm of claim 16, wherein the sensors support the rigid shell without being fixed to the rigid shell.

18. A robotic arm, comprising:
a link;
a rigid shell formed over the link; and
one or more sensors configured to detect contact between an external object and the rigid shell, a given sensor of the one or more sensors comprising at least one of:
  a load concentrator configured to control a point at which the rigid shell applies a force to the given sensor, or
  a flexure configured to scale a force applied to the given sensor and isolate the given sensor from shear forces.

19. The robotic arm of claim 18, wherein the given sensor comprises the load concentrator.

20. The robotic arm of claim 18, wherein the given sensor comprises the flexure.

* * * * *